(12) United States Patent
Balan et al.

(10) Patent No.: US 9,644,222 B2
(45) Date of Patent: *May 9, 2017

(54) METHODS FOR PRETREATING BIOMASS

(75) Inventors: Venkatesh Balan, East Lansing, MI (US); Bruce E Dale, Mason, MI (US); Shishir Chundawat, Piscataway, NJ (US); Leonardo Sousa, Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 211 days.

This patent is subject to a terminal disclaimer.

(21) Appl. No.: 13/997,043

(22) PCT Filed: Dec. 22, 2011

(86) PCT No.: PCT/US2011/066868
§ 371 (c)(1),
(2), (4) Date: Aug. 20, 2013

(87) PCT Pub. No.: WO2012/088429
PCT Pub. Date: Jun. 28, 2012

(65) Prior Publication Data
US 2014/0038243 A1    Feb. 6, 2014

Related U.S. Application Data

(63) Continuation of application No. 12/976,344, filed on Dec. 22, 2010, now Pat. No. 8,968,515, which is a continuation-in-part of application No. 11/901,336, filed on Sep. 17, 2007, now Pat. No. 7,915,017, which is a continuation-in-part of application No. PCT/US2007/010415, filed on Apr. 30, 2007, said application No. 12/976,344 is a continuation of application No. PCT/US2010/035826, filed on May 21, 2010.

(60) Provisional application No. 60/796,375, filed on May 1, 2006, provisional application No. 61/180,308, filed on May 21, 2009.

(51) Int. Cl.
*C12P 19/14* (2006.01)
*C12P 19/02* (2006.01)
*C08B 1/00* (2006.01)
*C12P 7/10* (2006.01)

(52) U.S. Cl.
CPC .............. *C12P 19/14* (2013.01); *C08B 1/003* (2013.01); *C12P 7/10* (2013.01); *C12P 19/02* (2013.01); *C12P 2201/00* (2013.01); *Y02E 50/16* (2013.01); *Y02P 30/20* (2015.11)

(58) Field of Classification Search
None
See application file for complete search history.

(56) References Cited

U.S. PATENT DOCUMENTS

| | | |
|---|---|---|
| 2,017,779 A | 10/1935 | Vosburgh |
| 2,548,192 A | 4/1951 | Berg |
| 3,259,501 A | 7/1966 | Ulrey |
| 3,306,006 A | 2/1967 | Urban |
| 3,707,436 A | 12/1972 | O'Connor |
| 3,920,419 A | 11/1975 | Schroeder et al. |
| 4,064,276 A | 12/1977 | Conradsen et al. |
| 4,153,435 A | 5/1979 | Fischer |
| 4,263,744 A | 4/1981 | Stoller |
| 4,287,162 A | 9/1981 | Scheibel |
| 4,356,196 A | 10/1982 | Hultquist |
| 4,370,351 A | 1/1983 | Harper |
| 4,461,648 A | 7/1984 | Foody |
| 4,526,791 A | 7/1985 | Young |
| 4,581,044 A | 4/1986 | Uno et al. |
| 4,589,334 A | 5/1986 | Andersen |
| 4,594,131 A | 6/1986 | Maier |
| 4,600,590 A | 7/1986 | Dale |
| 4,644,060 A | 2/1987 | Chou |
| 4,848,026 A | 7/1989 | Dunn-Coleman et al. |
| 4,986,835 A | 1/1991 | Uno et al. |
| 4,995,888 A | 2/1991 | Beaupre et al. |
| 5,025,635 A | 6/1991 | Rockenfeller et al. |

(Continued)

FOREIGN PATENT DOCUMENTS

| | | |
|---|---|---|
| AU | 756976 B2 | 1/2003 |
| CA | 2368872 A1 | 10/2000 |

(Continued)

OTHER PUBLICATIONS

Topic 3 R&D on Processes for Solid, Liquid and Gaseous Fuels From Biomass, 20th EU BC&E, 2012, 26 pages.
Extended Search Report received for European Patent Application No. 07776479.3, mailed on May 26, 2010, 6 pages.
Office Action received for European Patent Application No. 07776479.3, mailed on Dec. 5, 2012, 4 pages.
Office Action received for European Patent Application No. 07776479.3, mailed on May 30, 2012, 6 pages.
Office Action received for European Patent Application No. 10778488.6, mailed on Dec. 30, 2011, 2 pages.
Non Final Office Action received for U.S. Appl. No. 11/729,632, mailed on May 6, 2009, 5 pages.
Notice of Allowance received for U.S. Appl. No. 11/729,632, mailed on Nov. 16, 2009, 7 pages.
Restriction Requirement received for U.S. Appl. No. 11/897,119, mailed on Sep. 30, 2011, 6 pages.

(Continued)

*Primary Examiner* — Taeyoon Kim
*Assistant Examiner* — Srikanth Patury
(74) *Attorney, Agent, or Firm* — Clark IP Law, PLC

(57) ABSTRACT

A method for pretreating biomass is provided, which includes, in a reactor, allowing gaseous ammonia to condense on the biomass and react with water present in the biomass to produce pretreated biomass, wherein reactivity of polysaccharides in the biomass is increased during subsequent biological conversion as compared to the reactivity of polysaccharides in biomass which has not been pretreated. A method for pretreating biomass with a liquid ammonia and recovering the liquid ammonia is also provided. Related systems which include a biochemical or biofuel production facility are also disclosed.

18 Claims, 15 Drawing Sheets

(56) References Cited

U.S. PATENT DOCUMENTS

| | | |
|---|---|---|
| 5,037,663 A | 8/1991 | Dale |
| 5,047,332 A | 9/1991 | Chahal |
| 5,114,694 A | 5/1992 | Grotz, Jr. |
| 5,171,592 A | 12/1992 | Holtzapple et al. |
| 5,370,999 A | 12/1994 | Stuart |
| 5,473,061 A | 12/1995 | Bredereck et al. |
| 5,660,603 A | 8/1997 | Elliot et al. |
| 5,736,032 A | 4/1998 | Cox et al. |
| 5,865,898 A | 2/1999 | Holtzapple et al. |
| 5,939,544 A | 8/1999 | Karstens et al. |
| 6,027,552 A | 2/2000 | Ruck et al. |
| 6,106,888 A | 8/2000 | Dale et al. |
| 6,176,176 B1 | 1/2001 | Dale et al. |
| 6,255,505 B1 | 7/2001 | Bijl et al. |
| 6,416,621 B1 | 7/2002 | Karstens |
| 6,425,939 B1 | 7/2002 | Moreau et al. |
| 6,444,437 B1 | 9/2002 | Sporleder et al. |
| 6,524,848 B2 | 2/2003 | McNelly |
| 6,585,807 B2 | 7/2003 | Umino et al. |
| 6,620,292 B2 | 9/2003 | Wingerson |
| 6,872,296 B2 | 3/2005 | Kim |
| 6,893,484 B2 | 5/2005 | Thomas |
| 7,049,485 B2 | 5/2006 | Sticklen et al. |
| 7,187,176 B2 | 3/2007 | Lim et al. |
| 7,250,074 B2 | 7/2007 | Tonkovich et al. |
| 7,371,926 B2 | 5/2008 | Sticklen et al. |
| 7,371,962 B2 | 5/2008 | Zuppero et al. |
| 7,494,675 B2 | 2/2009 | Abbas et al. |
| 7,494,792 B2 | 2/2009 | Warzywoda et al. |
| 7,537,744 B2 | 5/2009 | Benderly et al. |
| 7,585,652 B2 | 9/2009 | Foody et al. |
| 7,771,565 B2 | 8/2010 | Kirov et al. |
| 7,910,338 B2 | 3/2011 | Hennessey et al. |
| 7,910,675 B2 | 3/2011 | Funk et al. |
| 7,915,017 B2 | 3/2011 | Dale |
| 7,937,851 B2 | 5/2011 | Rajagopalan et al. |
| 8,020,342 B2 | 9/2011 | Karpik |
| 8,030,030 B2 | 10/2011 | Varanasi et al. |
| 8,367,378 B2 | 2/2013 | Balan et al. |
| 8,394,177 B2 | 3/2013 | Campbell et al. |
| 8,394,611 B2 | 3/2013 | Dale et al. |
| 8,419,900 B2 | 4/2013 | Baba et al. |
| 8,444,925 B2 | 5/2013 | Baba |
| 8,551,549 B2 | 10/2013 | Zeeck |
| 8,651,403 B2 | 2/2014 | Camp et al. |
| 8,673,031 B2 | 3/2014 | Dale et al. |
| 8,771,425 B2 | 7/2014 | Dale |
| 8,846,123 B2 | 9/2014 | Zeeck |
| 8,945,245 B2 | 2/2015 | Bals et al. |
| 8,968,515 B2 | 3/2015 | Balan et al. |
| 8,980,599 B2 | 3/2015 | Tolan et al. |
| 9,039,792 B2 | 5/2015 | Dale et al. |
| 2003/0044951 A1 | 3/2003 | Sporleder et al. |
| 2005/0064577 A1 | 3/2005 | Berzin |
| 2006/0014260 A1 | 1/2006 | Fan et al. |
| 2006/0130396 A1 | 6/2006 | Werner |
| 2006/0177917 A1 | 8/2006 | Warzywoda et al. |
| 2007/0029252 A1* | 2/2007 | Dunson et al. ............... 210/603 |
| 2007/0031918 A1 | 2/2007 | Dunson, Jr. et al. |
| 2007/0037259 A1 | 2/2007 | Hennessey et al. |
| 2007/0113736 A1 | 5/2007 | Bandosz |
| 2007/0192900 A1 | 8/2007 | Sticklen |
| 2007/0202214 A1 | 8/2007 | Lewis et al. |
| 2007/0287795 A1 | 12/2007 | Huda et al. |
| 2008/0008783 A1 | 1/2008 | Dale |
| 2008/0057555 A1 | 3/2008 | Nguyen |
| 2008/0087165 A1 | 4/2008 | Wright et al. |
| 2008/0115415 A1 | 5/2008 | Agrawal et al. |
| 2008/0171297 A1 | 7/2008 | Reynolds et al. |
| 2008/0229657 A1 | 9/2008 | Senyk et al. |
| 2008/0256851 A1 | 10/2008 | Lumb |
| 2008/0264254 A1 | 10/2008 | Song et al. |
| 2008/0280236 A1 | 11/2008 | Wright |
| 2009/0011474 A1 | 1/2009 | Balan et al. |
| 2009/0042259 A1 | 2/2009 | Dale et al. |
| 2009/0049748 A1 | 2/2009 | Day et al. |
| 2009/0053770 A1 | 2/2009 | Hennessey et al. |
| 2009/0053771 A1 | 2/2009 | Dale et al. |
| 2009/0064569 A1 | 3/2009 | Khater et al. |
| 2009/0087898 A1 | 4/2009 | Haase et al. |
| 2009/0093027 A1 | 4/2009 | Balan et al. |
| 2009/0099079 A1 | 4/2009 | Emalfarb et al. |
| 2009/0123361 A1 | 5/2009 | Johannessen et al. |
| 2009/0178671 A1 | 7/2009 | Ahring et al. |
| 2009/0221042 A1 | 9/2009 | Dale et al. |
| 2009/0230040 A1 | 9/2009 | Limcaco |
| 2009/0313976 A1 | 12/2009 | Johannessen et al. |
| 2009/0318670 A1 | 12/2009 | Dale et al. |
| 2010/0159521 A1 | 6/2010 | Cirakovic et al. |
| 2010/0267999 A1 | 10/2010 | Lau et al. |
| 2010/0279361 A1 | 11/2010 | South et al. |
| 2011/0192559 A1 | 8/2011 | Venkatesh et al. |
| 2011/0201091 A1 | 8/2011 | Dale |
| 2011/0290114 A1 | 12/2011 | Campbell et al. |
| 2011/0300269 A1 | 12/2011 | Dale et al. |
| 2012/0064574 A1 | 3/2012 | Tokuyasu et al. |
| 2012/0071308 A1 | 3/2012 | Sekar |
| 2012/0085505 A1 | 4/2012 | Sabourin |
| 2012/0125548 A1 | 5/2012 | Cohen |
| 2012/0125551 A1 | 5/2012 | Cohen et al. |
| 2012/0187228 A1 | 7/2012 | Camp et al. |
| 2012/0325202 A1 | 12/2012 | Dale |
| 2013/0196398 A1 | 8/2013 | Bals et al. |
| 2013/0217073 A1 | 8/2013 | Chundawat et al. |
| 2013/0247456 A1 | 9/2013 | Dale et al. |
| 2013/0280762 A1 | 10/2013 | Dale et al. |
| 2013/0289268 A1 | 10/2013 | Teymouri et al. |
| 2014/0227757 A1 | 8/2014 | Jin et al. |
| 2015/0112101 A1 | 4/2015 | Bals et al. |
| 2015/0125907 A1 | 5/2015 | Balan et al. |

FOREIGN PATENT DOCUMENTS

| | | |
|---|---|---|
| CA | 2573046 A1 | 1/2006 |
| CA | 2610797 A1 | 12/2006 |
| CA | 2752604 A1 | 8/2010 |
| CA | 2797193 A1 | 10/2011 |
| CA | 2762985 C | 7/2013 |
| CA | 2 650 860 C | 9/2013 |
| CA | 2 737 704 C | 11/2013 |
| CA | 2760840 C | 12/2015 |
| CN | 101223273 A | 7/2008 |
| CN | 102597247 A | 7/2012 |
| CN | 102939388 A | 2/2013 |
| DE | 20301645 U1 | 4/2003 |
| EP | 0077287 A2 | 4/1983 |
| EP | 144930 A2 | 6/1985 |
| EP | 1247781 A2 | 10/2002 |
| EP | 1533279 A1 | 5/2005 |
| EP | 1690944 A1 | 8/2006 |
| EP | 2411492 A2 | 2/2012 |
| EP | 2561084 A2 | 2/2013 |
| EP | 2841588 A2 | 3/2015 |
| GB | 1310835 | 3/1973 |
| GB | 1381728 A | 1/1975 |
| GB | 2122864 A | 1/1984 |
| IN | 249187 | 10/2011 |
| IN | 9645/DELNP/2011 A | 2/2013 |
| JP | 2008-161125 A | 7/2008 |
| JP | 2008-535664 A | 9/2008 |
| JP | 2011-160753 A | 8/2011 |
| RU | 2215755 C1 | 11/2003 |
| WO | 85/00133 A1 | 1/1985 |
| WO | 00/61858 A1 | 10/2000 |
| WO | 01/32715 A1 | 5/2001 |
| WO | 02/37981 A2 | 5/2002 |
| WO | 2004/033920 A1 | 4/2004 |
| WO | 2005/091418 A2 | 9/2005 |
| WO | 2006/055362 A1 | 5/2006 |
| WO | 2006/128304 A1 | 12/2006 |
| WO | 2007/005918 A2 | 1/2007 |
| WO | 2007/005918 A3 | 8/2007 |
| WO | 2007/130337 A1 | 11/2007 |
| WO | 2008/020901 A2 | 2/2008 |

(56) References Cited

FOREIGN PATENT DOCUMENTS

| WO | 2008/114139 A2 | 9/2008 |
|---|---|---|
| WO | 2008/114139 A3 | 12/2008 |
| WO | 2009/058276 A1 | 5/2009 |
| WO | 2010/098408 A1 | 9/2010 |
| WO | 2010/121348 A1 | 10/2010 |
| WO | 2010/135679 A1 | 11/2010 |
| WO | 2010/147218 A1 | 12/2010 |
| WO | 2011/028543 A2 | 3/2011 |
| WO | 2011/046818 A2 | 4/2011 |
| WO | 2011/028543 A3 | 6/2011 |
| WO | 2011/080154 A1 | 7/2011 |
| WO | 2011/125056 A1 | 10/2011 |
| WO | 2011/133571 A2 | 10/2011 |
| WO | 2011/133571 A3 | 1/2012 |
| WO | 2012/012594 A1 | 1/2012 |
| WO | 2012/071312 A2 | 5/2012 |
| WO | 2012/088429 A2 | 6/2012 |
| WO | 2013/106113 A2 | 7/2013 |
| WO | 2013/131015 A1 | 9/2013 |
| WO | 2013/106113 A3 | 10/2013 |
| WO | 2013/163571 A2 | 10/2013 |
| WO | 2013/163571 A3 | 10/2013 |

OTHER PUBLICATIONS

Non Final Office Action received for U.S. Appl. No. 11/901,336, mailed on Apr. 27, 2010, 10 pages.
Notice of Allowance received for U.S. Appl. No. 11/901,336, mailed on Aug. 24, 2010, 5 pages.
Office Action received for European Patent Application No. 11162906.9, mailed on Jan. 16, 2012, 2 pages.
Office Action received for European Patent Application No. 11772569.7, mailed on Nov. 30, 2012, 2 pages.
Final Office Action received for U.S. Appl. No. 12/226,763, mailed on Jan. 10, 2012, 16 pages.
Non Final Office Action received for U.S. Appl. No. 12/226,763, mailed on Aug. 22, 2011, 13 pages.
Notice of Allowance received for U.S. Appl. No. 12/226,763, mailed on May 29, 2012, 9 pages.
Notice of Allowance received for U.S. Appl. No. 12/226,763, mailed on Oct. 1, 2012, 7 pages.
Final Office Action received for U.S. Appl. No. 12/229,225, mailed on Jan. 6, 2012, 7 pages.
Non Final Office Action received for U.S. Appl. No. 12/229,225, mailed on Aug. 16, 2011, 6 pages.
Notice of Allowance received for U.S. Appl. No. 12/286,913, mailed on Oct. 3, 2012, 9 pages.
Restriction Requirement received for U.S. Appl. No. 12/763,102, mailed on Sep. 17, 2012, 11 pages.
Notice of Allowance received for U.S. Appl. No. 12/976,344, mailed on Feb. 23, 2012, 7 pages.
Notice of Allowance received for U.S. Appl. No. 12/976,344, mailed on Mar. 27, 2012, 8 pages.
Non Final Office Action received for U.S. Appl. No. 13/202,011, mailed on Sep. 27, 2012, 8 pages.
Non Final Office Action received for U.S. Appl. No. 13/591,092, mailed on Dec. 13, 2012, 13 pages.
Office Action received for Canadian Patent Application No. 2,650,860, mailed on Jun. 18, 2012, 2 pages.
Office Action received for Canadian Patent Application No. 2,650,860, mailed on Oct. 24, 2011, 3 pages.
Office Action received for Canadian Patent Application No. 2,737,704, mailed on Jun. 4, 2012, 4 pages.
Office Action received for Canadian Patent Application No. 2,737,704, mailed on Nov. 5, 2012, 3 pages.
Office Action received for Canadian Patent Application No. 2,760,840, mailed on Aug. 6, 2012, 4 pages.
Office Action received for Canadian Patent Application No. 2,760,840, mailed on Mar. 28, 2012, 3 pages.
Office Action received for Canadian Patent Application No. 2,762,985, mailed on Jul. 6, 2012, 2 pages.
Office Action received for Canadian Patent Application No. 2,762,985, mailed on Mar. 13, 2012, 4 pages.
Office Action received for Chinese Patent Application No. 200780025394.4, mailed on Oct. 13, 2011, 7 pages of English Translation & 4 pages of Official Copy.
Office Action received for Chinese Patent Application No. 200780025394.4, mailed on Oct. 30, 2012, 3 pages (Official Copy only).
Office Action received for Australian Patent Application No. 2010249409, issued on Aug. 30, 2012, 4 pages.
Office Action received for Australian Patent Application No. 2010289797, issued on Oct. 30, 2012, 4 pages.
Office Action received for Chinese Patent Application No. 201110097994.X, issued on Jul. 30, 2012, 14 pages of English Translation & 11 pages of Official Copy.
Office Action received for Australian Patent Application No. 2011201768, issued on Jun. 21, 2012, 3 pages.
Adapa et al., "Compression Characteristics of Selected Ground Agricultural Biomass", Agricultural Engineering International: the CIGR Ejournal. Manuscript 1347, vol. XI, Jun. 2009, 19 pages.
Alizadeh et al., "Pretreatment of Switchgrass by Ammonia Fiber Explosion (AFEX)", Applied Biochemistry and Biotechnology, vol. 121-124, 2005, pp. 1133-1141.
Bergner et al., "Archives of Animal Nutrition", Arch. Tierernahrung, vol. 30, 1980, pp. 239-256.
Carolan, etal Technical and Financial Feasibility Analysis of Distributed Bioprocessing Using Regional Biomass Pre-Processing Centers, Journal of Agricultural & Food Industrial Organization, vol. 5, No. 2, Article 10, Explorations in Biofuels Economics, Policy, and History, 2007, 29 pages.
Cen et al., "Production of Cellulase by Solid-State Fermentation", Advances in Biochemical Engineering/Biotechnology, vol. 65, 1999, pp. 69-92.
Chahal, D.S., "Bioconversion of Hemicelluloses into Useful Products in an Integrated Process for Food/Feed and Fuel (Ethanol) Production form Biomass", Biotechnology and Bioengineering Symposium, No. 14, 1984, pp. 425-433.
Chahal et al., "Production of Cellulase in Solid-State Fermentation with Trichoderma reesei MCG 80 on Wheat Straw", Applied Biochemistry and Biotechnology, vol. 57/58, 1996, pp. 433-442.
Chang, Shu-Ting, "The World Mushroom Industry: Trends and Technological Development", International Journal of Medicinal Mushrooms, vol. 8, 2006, pp. 297-314.
Chinedu et al., "Xylanase Production of Aspergillus niger and Penicillium chrysogenum from Ammonia Pretreated Cellulosic Waste", Research Journal of Microbiology, vol. 3, No. 4, 2008, pp. 246-253.
Chundawat, Shishir Pratap Singh., "Ultrastructural and Physicochemical Modifications within Ammonia Treated Lignocellulosic Cell Walls and their Influence on Enzymatic Digestibility", 2010, 9 pages.
Deshusses, Marc A., "Biological Waste Air Treatment in Biofilters", Current Opinion in Biotechnology, vol. 8, 1997, pp. 335-339.
Non Final Office Action received for U.S. Appl. No. 12/286,913, mailed on Mar. 1, 2012, 7 pages.
Non Final Office Action received for U.S. Appl. No. 12/976,344, mailed on Apr. 5, 2013, 12 pages.
Advisory Action received for U.S. Appl. No. 12/763,102, mailed on Dec. 6, 2013, 3 pages.
Office Action received for Mexican Patent Application No. MX/a/2011/012357, mailed on Mar. 13, 2013, 1 page of English Translation.
International Search Report and Written Opinion received for PCT Patent Application No. PCT/US2007/010415, mailed on Oct. 11, 2007, 5 pages.
International Search Report and Written Opinion received for PCT Application No. PCT/US2010/046525, mailed on Apr. 29, 2011, 9 pages.
International Preliminary Report on Patentability received for PCT Application No. PCT/US2010/046525, issued on Feb. 28, 2012, 5 pages.

(56) References Cited

OTHER PUBLICATIONS

International Search Report and Written Opinion received for PCT Patent Application No. PCT/US2011/066868, mailed on Sep. 19, 2012, 6 pages.
Chundawat, "Ultrastructural and Physicochemical Modifications within Ammonia Treated Lignocellulosic Cell Walls and their Influence on Enzymatic Digestibility", Dissertation for Michigan State University, ProQuest, UMI Dissertation Publishing, 2009, 230 pages.
Eggeman et al., "Process and Economic Analysis of Pretreatment Technologies", Bioresource Technology, vol. 96, 2005, pp. 2019-2025.
Felix et al., "In Vitro and In Vivo Digestibility of Soya-Bean Straw Treated with Various Alkalis", Animal Production, vol. 51, No. 1, 1990, pp. 47-59.
Ferrer et al., "NR 06. Sugar Production from Rice Straw", Arch. Latinoam. Prod. Anim., vol. 5, No. 1, 1997, pp. 112-114.
Jain et al., "Effect of Ammonia Pretreatment on Switchgrass for Production of Cellulase using Trichoderma reesei Rut C-30", 31st Symposium on Biotechnology for Fuels and Chemicals, May 4, 2009, 1 page.
Kaliyan et al., "Roll Press Briquetting and Pelleting of Corn Stover and Switchgrass", Transactions of the ASABE, vol. 52, No. 2, 2009, pp. 543-555.
Kudra et al., "Superheated Steam Drying", Chapter 7, Advanced Drying Technologies, 2002, pp. 81-111.
Kumar et al., "Methods for Pretreatment of Lignocellulosic Biomass for Efficient Hydrolysis and Biofuel Production", Industrial & Engineering Chemistry Research, 2009, pp. A-Q.
Lynd et al., "Microbial Cellulose Utilization: Fundamentals and Biotechnology", Microbiology and Molecular Biology Reviews, vol. 66, No. 3, Sep. 2002, pp. 506-577.
Marshall et al., "Complete Rations for Dairy Cattle. II. Sugarcane Bagasse Pellets as Roughage in Blended Rations for Lactating Cows", Journal of Dairy Science, vol. 58, No. 6, Jun. 1975, pp. 896-900.
Miller, "Phase I Biomass Enhanced Refined Lignite Demonstration Project", Project, Dec. 15, 2008, 24 pages.
Mosier et al., "Features of Promising Technologies for Pretreatment of Lignocellulosic Biomass", Bioresource Technology, vol. 96, 2005, pp. 673-686.
Perry et al., "Reaction Kinetics and Reactor Design", Chemical Engineers' Handbook, Fourth Edition, 1963, pp. 4-21-4-24.
Roman-Ponce et al., "Complete Rations for Dairy Cattle. V. Interaction of Sugarcane Bagasse Quantity and Form with Soybean Meal, Urea, and Starea", Journal of Dairy Science, vol. 58, No. 9, Sep. 1975, pp. 1320-1327.
Sheridan et al., "Assessment of the Influence of Media Particle Size on the Biofiltration of Odorous Exhaust Ventilation Air from a Piggery Facility", Bioresource Technology, vol. 84, 2002, pp. 129-143.
Singhania et al., "Advancement and Comparative Profiles in the Production Technologies Using Solid-State and Submerged Fermentation for Microbial Cellulases", Enzyme and Microbial Technology, vol. 46, 2010, pp. 541-549.
Teymouri et al., "Optimization of the Ammonia Fiber Explosion (AFEX) Treatment Parameters for Enzymatic Hydrolysis of Corn Stover", Bioresource Technology, vol. 96, 2005, pp. 2014-2018.
Waiss et al., "Improving Digestibility of Straws for Ruminant Feed by Aqueous Ammonia", Journal of Animal Science, vol. 35, No. 1, 1972, pp. 109-112.
Warzywoda et al., "Production and Characterization of Cellulolytic Enzymes from Trichoderma reesei Grown on Various Carbon Sources", Bioresource Technology, vol. 39, 1992, pp. 125-130.
Wilson, "A Cost Analysis for the Densification and Transportation of Cellulosic Biomass for Ethanol Production", A Thesis, 2011, 86 pages.
Zhang et al., "The Effect of Different Treatment Conditions on Biomass Binder Preparation for Lignite Briquette", Fuel Processing Technology, vol. 73, 2001, pp. 185-196.
Zhu et al., "Cocurrent Downflow Circulating Fluidized Bed (Downer) Reactors—A State of the Art Review", The Canadian Journal of Chemical Engineering, vol. 73, Oct. 1995, pp. 662-677.
Zhong et al., "Optimization of Enzymatic Hydrolysis and Ethanol Fermentation from AFEX-Treated Rice Straw", Applied Microbiology and Biotechnology, vol. 84, No. 4, Sep. 2009, pp. 667-676.
Extended European Search Report received for European Patent Application No. 10814256.3, mailed on Jan. 23, 2013, 6 pages.
Official Communication pursuant to Article 94(3) EPC received for European Patent Application No. 10814256.3, mailed on Sep. 6, 2013, 4 pages.
Non-Final Office Action received for U.S. Appl. No. 11/719,158, mailed on Apr. 1, 2009, 6 pages.
Final Office Action received for U.S. Appl. No. 11/719,158, mailed on Aug. 4, 2010, 7 pages.
Notice of Allowance received for U.S. Appl. No. 11/719,158, mailed on Jan. 6, 2011, 4 pages.
Official Communication pursuant to Article 94(3) EPC received for European Patent Application No. 11162906.9, mailed on Mar. 6, 2013, 5 pages.
Extended European Search Report for European Patent Application No. 11850707.8, mailed on Jul. 3, 2014, 8 pages.
Notice of Allowance received for U.S. Appl. No. 12/226,763, mailed on Jan. 22, 2013, 7 pages.
Non Final Office Action received for U.S. Appl. No. 12/286,913, mailed on Sep. 28, 2011, 7 pages.
Non-Final Office Action received for U.S. Appl. No. 12/763,102, mailed on Dec. 24, 2012, 18 pages.
Final Office Action received for U.S. Appl. No. 12/763,102, mailed on Aug. 5, 2013, 12 pages.
Non-Final Office Action received for U.S. Appl. No. 12/791,703, mailed on Jul. 27, 2012, 7 pages.
Notice of Allowance received for U.S. Appl. No. 12/791,703, mailed on Nov. 8, 2012, 8 pages.
Non-Final Office Action received for U.S. Appl. No. 12/976,344, mailed on Apr. 1, 2014, 19 pages.
Restriction Requirement received for U.S. Appl. No. 13/202,011, mailed on Jul. 17, 2012, 6 pages.
Notice of Allowance received for U.S. Appl. No. 13/202,011, mailed on Apr. 9, 2013, 9 pages.
Supplemental Notice of Allowance received for U.S. Appl. No. 13/202,011, mailed on Nov. 8, 2013, 7 pages.
Notice of Allowance received for U.S. Appl. No. 13/458,830, mailed on Jul. 9, 2014, 8 pages.
Final Office Action received for U.S. Appl. No. 13/591,092, mailed on Mar. 25, 2013, 22 pages.
Advisory Action received for U.S. Appl. No. 13/591,092, mailed on Jun. 6, 2013, 3 pages.
Notice of Allowance received for U.S. Appl. No. 13/591,092, mailed on Feb. 21, 2014, 11 pages.
Office Action received for Canadian Patent Application No. 2,760,840, mailed on Jan. 3, 2013, 3 pages.
Office Action received for Canadian Patent Application No. 2,760,840, mailed on Jul. 30, 2013, 4 pages.
Office Action received for Chinese Patent Application No. 201110097994.X, mailed on Mar. 27, 2013, 7 pages of English Translation.
Patent Examination Report received for Australian Patent Application No. 2011348161, mailed on Feb. 21, 2014, 4 pages.
Office Action received for Chinese Patent Application No. 201210287568.7, mailed on Jul. 26, 2013, 3 pages of English Translation.
Examination Report received for Australian Patent Application No. 2013205681, mailed on Jun. 27, 2013, 4 pages.
Notice of Allowance received for Canadian Patent Application No. 2,650,860, mailed on Apr. 2, 2013, 1 page.
International Preliminary Report on Patentability received for PCT Patent Application No. PCT/US2007/010415, mailed on Nov. 1, 2008, 6 pages.
International Search Report and Written Opinion for PCT Patent Application No. PCT/US2011/038524, mailed on Feb. 9, 2012, 7 pages.

(56) References Cited

OTHER PUBLICATIONS

International Search Report and Written Opinion received for PCT Application No. PCT/US2012/059898, mailed Jul. 26, 2013, 11 pages.
International Preliminary Report on Patentability received for PCT Application No. PCT/US2011/066868, mailed Jul. 4, 2013, 5 pages.
International Search Report received for PCT Patent Application No. PCT/US2013/028689, mailed on Jun. 4, 2013, 5 pages.
International Search Report received for PCT Patent Application No. PCT/US2013/037935, mailed on Jul. 19, 2013, 4 pages.
Adapa et al., "Pelleting Characteristics of Selected Biomass With and Without Steam Explosion Pretreatment", International Journal of Agricultural and Biological Engineering, vol. 3, No. 3, Sep. 2010, pp. 62-79.
Balan et al., "Lignocellulosic Biomass Pretreatment Using AFEX", Biofuels: Methods and Protocols, Methods in Molecular Biology, Chapter 5, vol. 581, 2009, pp. 61-77.
Bals et al., "Enzymatic Hydrolysis of Distiller's Dry Grain and Solubles (DDGS) Using Ammonia Fiber Expansion Pretreatment", Energy and Fuels 2006, vol. 20, No. 6, 2006, pp. 2732-2736.
Bals et al., "Evaluating the impact of Ammonia Fiber Expansion (AFEX) Pretreatment Conditions on the Cost of Ethanol Production", Bioresource Technology, vol. 102, 2011, pp. 1277-1283.
Chundawat et al., "Effect of Particle Size Based Separation of Milled Corn Stover on AFEX Pretreatment and Enzymatic Digestibility", Biotechnology and Bioengineering, vol. 96, No. 2, Feb. 1, 2007, pp. 219-231.
Chundawat et al., "Multi-scale Visualization and Characterization of Lignocellulosic Plant Cell Wall Deconstruction During Thermochemical Pretreatment", Energy & Environmental Science, No. 4, 2011, pp. 973-984.
Cosgrove, Daniel J., "Growth of the Plant Cell Wall", Nature Reviews Molecular Cell Biology, vol. 6, Nov. 2005, pp. 850-861.
Dale et al., "Extrusion Processing for Ammonia Fiber Explosion (AFEX)", Applied Biochemistry and Biotechnology, vol. 77-79, 1999, pp. 35-45.
Dale et al., "Fermentation of Lignocellulosic Materials Treated by Ammonia Freeze-Explosion", Reprinted from Developments in Industrial Microbiology, vol. 26, Chapter 13, 1985, pp. 223-233.
Erickson, David, "Edible Fats and Oils Processing—Basic Principles and Modern Practices", AOCS Press, Netherlands, 1990, 6 pages.
Fulks et al., "A Review of Solid Materials as Alternative Ammonia Sources for Lean NOx Reduction with SCR", Technical Paper No. 2009-01-0907, SAE International, 2009, 13 pages.
Gao et al., "Mixture Optimization of Six Core Glycosyl Hydrolases for Maximizing Saccharification of Ammonia Fiber Expansion (AFEX) Pretreated Corn Stover", Bioresource Technology, vol. 101, No. 8, Apr. 2010, pp. 2770-2781.
Hanchar et al., "Separation of Glucose and Pentose Sugars by Selective Enzyme Hydrolysis of AFEX-Treated Corn Fiber", Applied Biochemistry and Biotechnology, vol. 136-140, 2007, pp. 313-325.
Jin et al., "A Novel Integrated Biological Process for Cellulosic Ethanol Production Featuring High Ethanol Productivity, Enzyme Recycling and Yeast Cells Reuse", Energy and Environmental Science, 2012, No. 5, The Royal Society of Chemistry, 2012, 8 pages.
Jin et al., "Two-Step SSCF to Convert AFEX-Treated Switchgrass to Ethanol using Commerical Enzymes and *Saccharomyces cerevisiae* 424A (LNH-ST)", Bioresource Technology, vol. 101, No. 21, 2010, pp. 8171-8178.
Kawasaki et al., "Deodorization of Ammonia by Coffee Grounds", Journal of Oleo Science, vol. 55, No. 1, 2006, pp. 31-35.
Kim et al., "Lime Pretreatment and Enzymatic Hydrolysis of Corn Stover", Bioresource Technology, vol. 96, No. 18, Mar. 10, 2005, pp. 1994-2006.
Kim et al., "Pretreatment and Fractionation of Corn Stover by Ammonia Recycle Percolation Process", Bioresource Technology, vol. 96, No. 18, 2005, pp. 2007-2013.
Kim et al., "Pretreatment of Corn Stover by Low-Liquid Ammonia Recycle Percolation Process", Applied Biochemistry and Biotechnolology, vol. 133, Apr. 2006, pp. 41-57.
Kumar et ei., "Does Densification Influence the Steam Pretreatment and Enzymatic Hydrolysis of Softwoods to Sugars?", Bioresource Technology, 2012, 38 pages.
Ladisch et al., "Building a Bridge to the Ethanol Industry—Follow-Up Project", National Renewable Energy Laboratory, Subcontractor Report, NREL/SR-510-33894, Apr. 2003, 36 pages.
Lau et al., Cellulosic Ethanol Production from AFEX-Treated Corn Stover Using *Saccharomyces cerevisiae* 424A (LNH-ST), PNAS, vol. 106, No. 5, Feb. 3, 2009, pp. 1368-1373.
Lau et al., "Ethanol Fermentation of *E. coli* KO11 in Hydrolysate from AFEX-treated Corn Stover", Biomass Conversion Research Laboratory, Department of Chemical Engineering and Materials Science, Apr. 30, 2006, 1 page.
Lau et al., "The Impacts of Pretreatment on the Fermentability of Pretreated Lignocellulosic Biomass: A Comparative Evaluation between Ammonia Fiber Expansion and Dilute Acid Pretreatment", Biotechnology for Biofuels, vol. 2, No. 30, 2009, 11 pages.
Laureano-Perez et al., "Understanding Factors that Limit Enzymatic Hydrolysis of Biomass—Characterization of Pretreated Corn Stover", Applied Biochemistry and Biotechnology, vol. 121-124, 2005, pp. 1081-1099.
Liu et al., "Partial Flow of Compressed-Hot Water through Corn Stover to Enhance Hemicellulose Sugar Recovery and Enzymatic Digestibility of Cellulose", Bioresource Technology, vol. 96, No. 18, 2005, pp. 1978-1985.
Lloyd et al., "Combined Sugar Yields for Dilute Sulfuric Acid Pretreatment of Corn Stover Followed by Enzymatic Hydrolysis of the Remaining Solids", Bioresource Technology, vol. 96, No. 18, Dec. 2005, pp. 1967-1977.
Lu et al., "Cellulose Adsorption and an Evaluation of Enzyme Recycle During Hydrolysis of Steam-Exploded Softwood Residues", Applied Biochemistry and Biotechnology, vol. 98-100, 2002, pp. 641-654.
Mani et al., "Economics of Producing Fuel Pellets from Biomass", Applied Engineering in Agriculture, vol. 22, No. 3, 2006, pp. 421-426.
Mosier et al., "Optimization of pH Controlled Liquid Hot Water Pretreatment of Corn Stover", Bioresource Technology, vol. 96, 2005, pp. 1986-1993.
Paul et al., "Liquid-Vapor Interfacial Properties of Water-Ammonia Mixtures: Dependence on Ammonia Concentration", The Journal of Chemical Physics, vol. 123, 2005, 10 pages.
Piva et al., "Detoxification Methods of Aflatoxins. A Review", Nutrition Research, vol. 15, No. 5, May 1995, pp. 767-776.
Prévot-D'Alvise et al., "Development of a Pilot Process for the Production of Alfalfa Peptide Isolate", Journal of Chemical Technology and Biotechnology, vol. 78, No. 5, May 2003, pp. 518-528.
Rijal et al., "Combined Effect of Pelleting and Pretreatment on Enzymatic Hydrolysis of Switchgrass", Bioresource Technology, vol. 116, 2012, pp. 36-41.
Rollin et al., "Increasing Cellulose Accesibility is More Important Than Removing Lignin: A Comparison of Cellulose Solvent-Based Lignocellulose Fractionation and Soaking in Aqueous Ammonia", Biotechnology and Bioengineering, vol. 108, No. 1, Jan. 1, 2011, pp. 22-30.
Selig et al., "Enzymatic Saccharification of Lignocellulosic Biomass", National Renewable Energy Laboratory, Technical Report, NREL/TP-510-42629, Mar. 21, 2008, 8 pages.
Sendich et al., "Recent Process Improvements for the Ammonia Fiber Expansion (AFEX) Process and Resulting Reductions in Minimum Ethanol Selling Price", Bioresource Technology, vol. 99, 2008, pp. 8429-8435.
Sokhansanj et al., "Biomass Densification—Cubing Operation and Costs for Corn Stover", Applied Engineering in Agriculture, vol. 20, No. 4, 2004, pp. 495-499.
Somerville et al., "Toward a Systems Approach to Understanding Plant Cell Walls", Science, vol. 306, No. 5705, Dec. 24, 2004, pp. 2206-2211.

(56) References Cited

OTHER PUBLICATIONS

Steele et al., "Enzyme Recovery and Recycling Following Hydrolysis of Ammonia Fiber Explosion-Treated Corn Stover", Applied Biochemistry and Biotechnology, vol. 121-124, No. 1-3, 2005, pp. 901-910.
Sunopta Bioprocess Group, "SunOpta BioProcess Solutions", SunOpta, 2838 Bovaird Drive West, Norval, Ontario L7A 0H2, bioprocess@sunopta.com, 2007, 20 pages.
Tabil et al., "Biomass Feedstock Pre-Processing—Part 1: Pre-Treatment", Biofuel's Engineering Process Technology, Chapter 18, Aug. 2011, pp. 411-438.
Tanner Industries, Inc., "Anhydrous Ammonia", Customer Manual, Dec. 2006, 17 pages.
Teymouri et al., "Hydrolysis of Ground and Unground AFEX Treated Corn Stover with Different Combinations of Cellulose and Xylanase", 27th Symposium on Biotechnology for Fuels and Chemicals. May 1-4, 2005, 21 pages.
Theerarattananoon et al., "Effects of the Pelleting Conditions on Chemical Composition and Sugar Yield of Corn Stover, Big Bluestem, Wheat Straw, and Sorghum Stalk Pellets", Bioprocess and Biosystems Engineering, vol. 35, No. 4, 2011, pp. 615-623.
Tolan, Jeffrey S., "Iogen's Demonstration Process for Producing Ethanol from Cellulosic Biomass", Chapter 9, Fuel-oriented Biorefineries, Biorefineries—Industrial Processes and Products, WILEY-VCH Verlag GmbH and Co., 2006, pp. 193-208.
Van Horn et al., "Complete Rations for Growing Dairy Replacements Utilizing By-Product Feedstuffs", Journal of Dairy Science, vol. 63, 1980, pp. 1465-1474.
Walter et al., "Industrial Uses of Biomass Energy—New Technologies for Modern Biomass Energy Carriers", Taylor and Francis, Chapter 9, edited by Rosillo-Calle F., Bajay SV, Rothman H, 2000, pp. 200-253.
Wang et al., "Cost Estimates and Sensitivity Analyses for the Ammonia Fiber Explosion Process", Applied Biochemistry and Biotechnology, vol. 70-72, No. 1, 1998, pp. 51-66.
Non Final Office Action received for U.S. Appl. No. 14/251,921, mailed on Nov. 16, 2015, 12 pages.
Non Final Office Action received for U.S. Appl. No. 13/835,382, mailed on Oct. 7, 2015, 10 pages.
Restriction Requirement received for U.S. Appl. No. 14/251,921 mailed on Sep. 3, 2015, 6 pages.
Notice of Allowance received for U.S. Appl. No. 13/835,766, mailed on Oct. 2, 2014, 8 pages.
Notice of Allowance received for U.S. Appl. No. 13/835,766, mailed on Jan. 28, 2015, 7 pages.
Notice of Allowance received for U.S. Appl. No. 12/976,344, mailed on Nov. 28, 2014, 10 pages.
Notice of Allowance received for U.S. Appl. No. 13/458,830, mailed on Dec. 18, 2014, 5 pages.
Office Action received for Canadian Patent Application No. 2,822,644, mailed on Sep. 8, 2014, 2 pages.
Office Action received for Canadian Patent Application No. 2,870,758, mailed on Jul. 24, 2015, 6 pages.
Office Action received for Chinese Patent Application No. 201180062555.3, mailed on Oct. 14, 2014, 9 pages of English translation and 8 pages of Official Notice.
Office Action received for Chinese Patent Application No. 201210287568.7, mailed on Nov. 4, 2014, 3 pages of English translation and 3 pages of Official Notice.
Office Action received for Mexican Patent Application No. MX/a/2014/012737, mailed on Dec. 23, 2014, 7 pages.
Office Action received for Vietnamese Patent Application No. 1-2014-03985, mailed on Feb. 13, 2015, 2 pages.
Preliminary Rejection received for Brazilian Patent Application No. PI0711139-8, mailed on Sep. 29, 2015, 11 pages.
Preliminary Rejection received for Brazilian Patent Application No. PI0722418-4, mailed on Sep. 29, 2015, 6 pages.
Extended European Search Report received for European Patent Application No. 14174649.5, mailed on Dec. 23, 2014, 8 pages.
Official Communication Pursuant to Article 94(3) EPC received for European Patent Application No. 14174649.5, mailed on Sep. 30, 2015, 5 pages.
Dale et al., "Hydrolysis of Lignocellulosics at Low Enzyme Levels: Application of the AFEX Process", Bioresource Technology, vol. 56, Apr. 1996, pp. 111-116.
Communication Pursuant to Article 94(3) EPC received for European Patent Application No. 10778488.6, mailed on Dec. 16, 2014, 4 pages.
Extended Search Report received for European Patent Application No. 15171198.3, mailed on Sep. 16, 2015.
Canadian Patent Document 2,752,604, Canadian Patents Database, Aug. 12, 2011, 12 pages.
Notice of Allowance Received for Canadian Patent Application No. 2,819,456, mailed on May 6, 2015, 3 pages.
Office Action Received for Chinese Patent Application No. 201080022215.3, mailed on Nov. 24, 2015, (4 pages of English Translation and 3 pages of Official Copy).
Office Action received for Chinese Patent Application No. 201080022215.3, mailed on Apr. 16, 2014, (3 pages of Official Notice and 4 pages of English translation).
Office Action received for Chinese Patent Application No. 201080022215.3, mailed on May 5, 2015, 9 pages (5 pages of English Translation and 4 pages of Official Copy).
Office Action received for Chinese Patent Application No. 201080022215.3, mailed on Nov. 6, 2014, (9 pages of English translation and 7 pages of Official Notice).
First Examination Report received for India Patent Application No. 9645/DELNP/2011, mailed on Jan. 20, 2016, 4 pages.
International Search Report and Written Opinion received for PCT Patent Application No. PCT/US10/35826, mailed on Jul. 13, 2010, 8 pages.
Preliminary Rejection received for Brazilian Patent Application No. PI0722418-4, mailed on Feb. 5, 2016, (English Translation only), 4 pages.

* cited by examiner

METHODS FOR PRETREATING BIOMASS

STATEMENT OF GOVERNMENT RIGHTS

This invention was made with government support under XCO-3-33033-01 awarded by the U.S. Department of Energy and under 00-52104-9663 awarded by the U.S. Department of Agriculture. The government has certain rights in the invention.

This application is a U.S. National Stage Filing under 35 U.S.C. 371 from International Application No. PCT/US2011/066868 filed on Dec. 22, 2011, and published in English as WO 2012/088429 on Jun. 28, 2012, which application claims priority to U.S. application Ser. No. 12/976,344, filed on Dec. 22, 2010, now issued as U.S. Pat. No. 8,968,515, which application is a continuation-in-part of U.S. application Ser. No. 11/901,336, filed on Sep. 17, 2007, now issued as U.S. Pat. No. 7,915,017, which application is a continuation-in-part of International Application No. PCT/US07/10415, filed on Apr. 30, 2007, which application claims the benefit of U.S. Provisional Application Ser. No. 60/796,375, filed on May 1, 2006, all of which are hereby incorporated by reference herein in their entireties. U.S. application Ser. No. 12/976,344 is also a continuation of International Application No. PCT/US2010/035826, filed on May 21, 2010, and published in English as WO 2010/135679 on Nov. 25, 2010, which application claims the benefit of U.S. Provisional Application Ser. No. 61/180,308, filed on May 21, 2009, both of which are hereby incorporated by reference herein in their entireties.

BACKGROUND

There is growing interest in using renewable feedstocks for manufacturing biofuels, such as bioethanol, biochemicals, and animal feed. Such products can be produced from lignocellulosic biomass ("biomass") using chemical and biochemical processes, such as acid catalysis, enzymatic catalysis, fermentation and animal digestion. However, lignocellulosic fibers in the biomass comprise a complex network of structural carbohydrates (i.e., polysaccharides) containing cellulose, hemicellulose and lignin, which are difficult to extract. As such, pretreatment of the biomass is needed to increase the rate and/or yield at which monosaccharide moieties and/or soluble sugar oligomers within the structural carbohydrates are subsequently obtained.

However, pretreatment attempts to date have fallen short of the desired economic and technical performance. For example, certain types of pretreatments degrade some of the sugars, thus reducing yields and inhibiting subsequent biological conversion of the remaining sugars. Additionally, when chemicals are used in pretreatment, they can be difficult to recover at a reasonable cost. Residual chemicals can also negatively affect downstream conversion operations. The effectiveness of many pretreatments is limited, such that the ultimate conversions of structural carbohydrates obtained, independent of lost yield by sugar degradation reactions, is inadequate for competitive process economics.

Inexpensive polysaccharides from renewable plant biomass can become the basis of chemical and fuels industries, replacing or substituting petroleum and other fossil-fuel feedstocks. Highly reactive lignocellulosic biomass can also become the basis of improved animal feeds, particularly for ruminant animals. However, effective, economical pretreatments are needed to make these polysaccharides available at a sufficiently high yield and acceptable cost.

SUMMARY

The embodiments described herein include a method (continuous, batch or semi-continuous batch) for treating biomass comprising, in a reactor, allowing ammonia to contact the biomass and react with water present in the biomass to produce pretreated biomass, wherein reactivity of polysaccharides in the biomass is increased during subsequent biological conversion as compared to polysaccharides in biomass which has not been pretreated. In one embodiment the ammonia is liquid ammonia and the method comprises an ammonia fiber expansion (APEX) pretreatment which includes a novel ammonia recovery method. In one embodiment, the ammonia is gaseous ammonia which condenses on the biomass in a gaseous ammonia process (GAP), such that, in one embodiment, the biomass is substantially uniformly pretreated by the gaseous ammonia.

In one embodiment, a method for treating biomass is provided, comprising: in a reactor, allowing gaseous ammonia to condense on the biomass and react with water present in the biomass to produce pretreated biomass, wherein reactivity of polysaccharides in the biomass is increased during subsequent biological conversion, such as enzyme hydrolysis or ruminant digestion as compared to polysaccharides in biomass which has not been pretreated. In one embodiment, the method further comprises delivering the gaseous ammonia to the reactor. In one embodiment, water can be optionally added to the biomass. In one embodiment, the polysaccharides contain hemicellulose and cellulose, the subsequent biological conversion is hydrolysis (e.g., enzymatic hydrolysis) or ruminant digestibility, and the reactivity of the polysaccharides is at least about 60% conversion of the hemicellulose and about 70% of cellulose to fermentable sugars within 24 hr or less.

In various embodiments, the reactor has a reactor temperature which increases instantaneously, such as substantially instantaneously, when the water and gaseous ammonia react, such as between about 25° C. and about 200° C., or between about 100° C. and about 140° C. In various embodiments, the gaseous ammonia is delivered to the reactor at a pressure between about 6.8 atm and about 68 atm, or between about 6.8 atm and about 20.4 atm.

In various embodiments, more than about 29.5% up to about 80% of glucan and xylan is converted to glucose and xylose within three days or less. In various embodiments, the biomass has a water or moisture content (MC) from about 5% to about 233% on a dry weight basis (dwb), or from about 5% to about 100% (dwb), such as from about 5% to about 60% dwb.

The residence or reaction time can vary, depending on the temperature, which varies depending on the pressure. In one embodiment, the gaseous ammonia reacts with the water in the biomass for about 1 minute to about 36 hours, or about 1 minute to about 120 minutes. In one embodiment, the residence time is only about 1 to about 15 min, such as between about 5 and 15 min, including any ratio there between.

The method can further comprise, in various embodiments, delivering a carrier gas to the reactor and combining the carrier gas with the gaseous ammonia before or after the gaseous ammonia is delivered to the reactor. The carrier gas can be oxidative (e.g., pure oxygen, air, etc.), an inert gas (e.g., nitrogen, argon, etc.) or steam.

The reactor can comprise any suitable type of reactor capable of carrying out the desired reaction. In one embodiment, the reactor is a fluidized bed reactor. In other embodiments, the reactor is a fixed bed reactor or a semi-fluidized bed reactor.

In various embodiments, the method can further comprise recycling at least a portion of the gaseous ammonia.

The method can further comprise, in one embodiment, a method for treating biomass comprising, in a reactor, impregnating biomass with an amount of ammonia, delivering a gaseous carrier at an elevated temperature to the reactor; and allowing the gaseous carrier to remove residual ammonia in the biomass to produce a pretreated biomass substantially free from ammonia, wherein the amount of ammonia is reduced as compared to reacting the ammonia and water without the gaseous carrier. The pretreated biomass can then be removed from the reactor.

Broadly, the various embodiments comprise delivering ammonia at an elevated temperature to a reactor; and allowing the gaseous ammonia to contact the biomass and react with water present in the biomass, wherein reactivity of polysaccharides in the biomass is increased during biological conversion as compared to polysaccharides in biomass which has not been pretreated. In one embodiment, the ammonia is gaseous ammonia which condenses on the biomass. In one embodiment, the ammonia is liquid ammonia and the ammonia vapor is recovered by cooling ammonia vapor produced after pretreated biomass containing the ammonia is subjected to high pressure steam in an ammonia column; providing the ammonia vapor to a mixer; adding water to the mixer to produce an ammonia-water mixture; condensing the ammonia-water mixture to produce a condensed, ammonia-water mixture; pressurizing the condensed ammonia-water mixture to produce a pressurized, condensed ammonia-water mixture; heating the pressurized, condensed ammonia-water mixture to produce a heated ammonia-water mixture.

In one embodiment, a system is provided, comprising a biofuel or biochemical production facility; and a reactor at an elevated temperature containing biomass and ammonia, the biomass containing polysaccharides, wherein the reactor is adapted to allow the ammonia to contact the biomass and react with water present in the biomass to increase reactivity of the polysaccharides. In one embodiment, the ammonia can be gaseous ammonia which condenses on the biomass and the system further comprises an ammonia recovery system or liquid ammonia and the system further comprises an ammonia recovery system.

Such an ammonia recovery system can comprise, in one embodiment, a first condenser adapted to cool ammonia vapor produced after pretreated biomass containing the ammonia is subjected to high pressure steam in an ammonia column; a mixer adapted to mix the ammonia vapor and added water to produce an ammonia-water mixture; one or more additional condensers for condensing the ammonia-water mixture and one or more pumps to pressurize the ammonia-water mixture to produce a condensed, pressurized ammonia-water mixture; and a heater for heating the ammonia-water mixture to produce a heated ammonia-water mixture.

The systems and methods described herein are applicable to a wide range of industries which produce various types of biofuels and biochemical, as well as animal feed. The various embodiments provide a highly reactive biomass efficiently and economically.

DETAILED DESCRIPTION OF THE EMBODIMENTS

Figure 1:
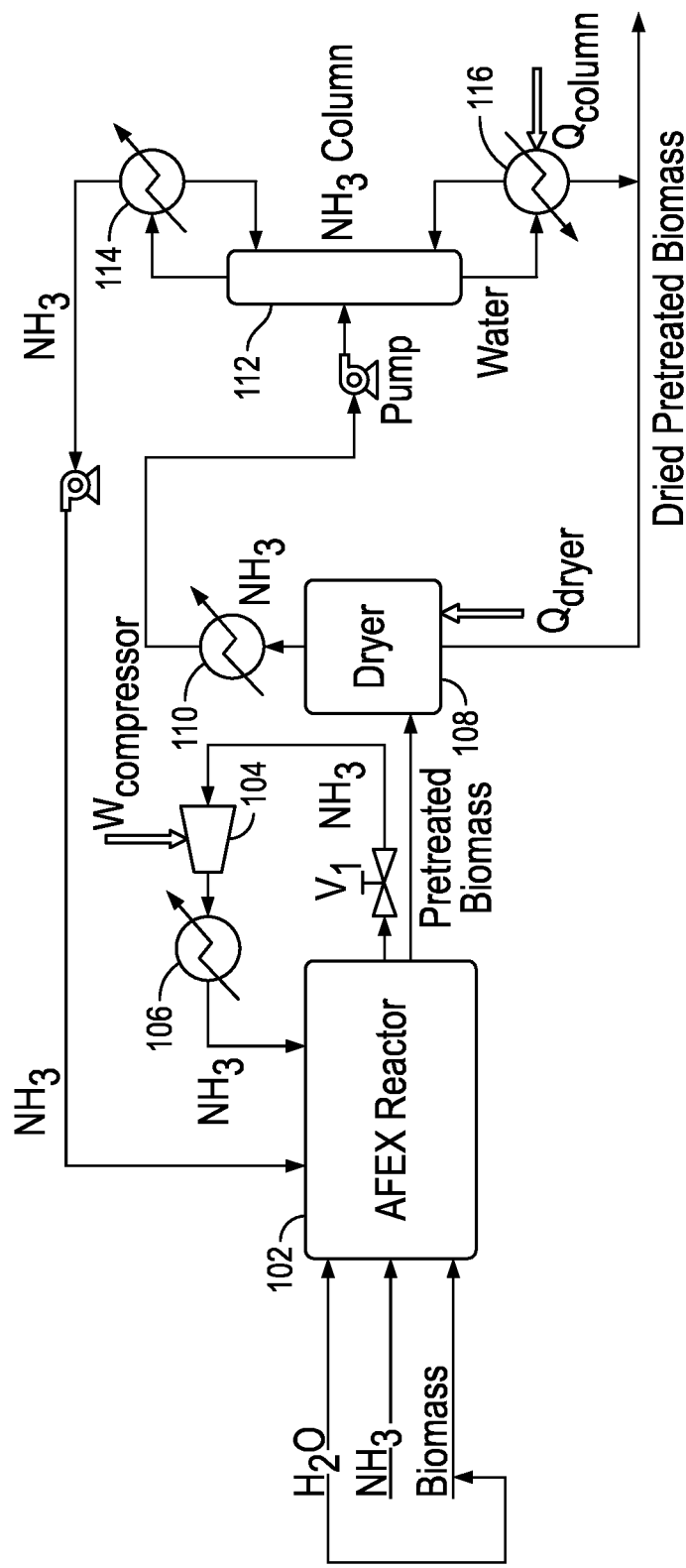
FIG. 1 is a process flow diagram for a conventional ammonia fiber expansion (AFEX) pretreatment with ammonia recovery and recycling.

In the following detailed description of embodiments of the invention, embodiments are described in sufficient detail to enable those skilled in the art to practice them, and it is to be understood that other embodiments may be utilized and that chemical and procedural changes may be made without departing from the spirit and scope of the present subject matter. The following detailed description is, therefore, not to be taken in a limiting sense, and the scope of embodiments of the present invention is defined only by the appended claims.

Lignocellulosic biomass (hereinafter "biomass") contains large amounts of structural carbohydrates (cellulose, hemicellulose, and the like) that can provide much less expensive simple sugars for fermentation or non-biological transformation to a variety of products or as improved animal feeds. However, the monosaccharide moieties contained therein are difficult to access.

The embodiments described herein include a method for treating biomass comprising delivering ammonia at an elevated temperature to a reactor; and allowing the ammonia to contact the biomass and react with water present in the biomass, wherein reactivity of polysaccharides in the biomass is increased during subsequent biological conversion as compared to polysaccharides in biomass which has not been pretreated. In one embodiment the ammonia is liquid ammonia and the method comprises an optimized ammonia fiber expansion (AFEX) pretreatment which includes a novel ammonia recovery method. In one embodiment, the ammonia is gaseous ammonia which condenses on the biomass in a gaseous ammonia process (GAP).

The Detailed Description that follows begins with a definition section followed by a brief overview of ammonia pretreatments, a description of the embodiments, an example section and a conclusion.

DEFINITIONS

The term "ammonia" as used herein refers to a compound of nitrogen and hydrogen with the formula $NH_3$. Ammonia can be in a gaseous, liquid (including a diluted liquid, such as ammonium hydroxide) or supercritical state.

The terms "biomass" or "lignocellulosic biomass" as used herein refers to an organic material derived from lignin, cellulose and hemicellulose, such as wood, plants, and organic wastes (e.g., alfalfa, wheat straw, corn stover, wood fibers) that can be converted into a biofuel.

The term "gaseous" as used herein refers to the state of matter distinguished from the solid and liquid states by density, viscosity and/or expansion.

The term "structural carbohydrates" as used herein refers to polysaccharide materials containing monosaccharide moieties available by hydrolysis.

The term "semi-continuous batch" as used herein refers to a process using more than one reactor, with each reactor fed a given amount of biomass in sequence.

The term "gas" as used herein is also intended to include any type of vapor.

The term "reactivity" as used herein refers generally, to the rate at which hemicellulose and cellulose in the polysaccharide materials (i.e., plant polymers) contained in biomass can be converted to fermentable sugars during a subsequent biological conversion (e.g., hydrolysis, ruminant digestion).

Ammonia Pretreatment Overview

Without pretreatment, biomass can exhibit low reactivity and digestibility. Corn stover, for example, has only a 25% glucan conversion even after 168 hrs. (e.g., Experiments done at 15 mg/g glucan enzyme loading for 24 hours at 50° C.; Optimal Enyme Coktail: 66.67% Ctec 2+16.66% Htec 2+16.66% Multifect pectinase), i.e., less than about 29.5% conversion of glucan over 168 hr (See Table 1, Expt 20c).

As a result, ammonia pretreatment processes are used. Ammonia pretreatment and recovery processes generate ammonia and water mixtures of differing phases, compositions and temperatures. The resulting ammonia and water mixtures can therefore potentially be combined together and mixed with additional biomass to provide for further pretreatment of the biomass.

Conventional ammonia pretreatment processes include ammonia recycle percolation (ARP) which includes a high severity, low contact time process, and a soaking in aqueous ammonia (SAA), which is a low severity, high contact time process. The range of expected reaction conditions in these methods are 60-180° C. and 5-15% $NH_3$, with the upper limit of the pressure being about 30 kg/cm$^2$ or 450 psi (30.6 atm).

With respect to ARP, aqueous ammonia (ammonium hydroxide) is used as the pretreatment reagent; a high-severity treatment (180° C., 15% ammonia, 450 psi (30.6 atm)) condition is used to limit the reaction time within 20 min; a packed-bed flow-through type of percolation reactor is employed and operated under a recirculation mode; and although most of the ammonia input to the process is recovered and reused, the ammonia equivalent to 2-5% of dry biomass is irreversibly consumed during the pretreatment process.

SAA is a batch process applied under low-severity condition. Because of lower severity, longer treatment time is required. At a typical condition of 15% $NH_3$ and 60° C., which gives the system pressure of near 1 atm, a reaction time of several hours is required to achieve an acceptable level of pretreatment effects. In order to attain an acceptable level of delignification and to prevent lignin recondensation, a liquid-to-solid ratio of 4 or higher is normally required in the SAA process. Because of low process energy and low equipment cost, the overall processing cost of SAA is substantially lower than that of ARP. On the other hand, SAA as a pretreatment process has limited application to particular feedstocks.

In another prior art process, an aqueous solution comprising ammonia may be derived from ammonia gas, ammonium hydroxide, urea and combination. Ammonia concentration is about 6-12 weight percent relative to dry weight of biomass and the dry weight of biomass is at a high solids concentration of at least about 15 weight percent relative to the weight of the biomass-aqueous ammonia mixture. The ammonia and biomass may react in the process at a temperature between 4° C. and about 200° C. A plasticizer softening agent (polyols, glycerol ethers, ethanol and ethanolamines) or combination may be used. Ammonia can also be recycled to the pretreatment reactor during pretreatment or following pretreatment. The aqueous solution comprising ammonia may optionally comprise at least one additional base such as NaOH, $NaCO_3$, KOH, $K_2CO_3$, $Ca(OH)_2$ and $CaCO_3$. The dry weight of biomass is at an initial concentration of at least about 15% up to about 80% of the weight of the biomass-aqueous ammonia mixture. Pretreatment can be done using an autoclave using steam gun. The reaction is performed in non-oxidative conditions (i.e., removing air from the reactor by applying vacuum). The reaction time is from about 8 to about 25 hr. Reaction temperature and residence time is correlated. Ammonia is removed from the reactor by applying vacuum and by neutralizing the pH using acid.

As can be seen, many known ammonia pretreatment methods pretreatment temperatures sufficiently high to degrade protein and negatively impact the ability of animals to digest amino acids, such as lysine, present in the final product. Yet other processes, such as conventional gaseous ammoniation, include extremely long residence times (up to weeks), and are expensive and inconvenient to scale-up. Supercritical ammonia based pretreatments are highly energy intensive and do not provide an economically-viable option.

Although still energy intensive, conventional ammonia fiber expansion (AFEX) is an alkaline pretreatment process which offers an improvement over other conventional ammonia pretreatments. In an AFEX process, the cell wall ultra-structure is modified without physically extracting lignin and hemicellulose into a separate liquid stream. In addition, the inhibitory compounds formed during the ammonia pretreatment process are insignificant as compared to a dilute acid pretreatment. See, for example, U.S. Pat. Nos. 5,037,663; 4,600,590; 4,600,590; and 5,037,663.

FIG. 1 shows a conventional AFEX system 100 for performing a conventional AFEX process, which includes use of a closed AFEX reactor (hereinafter "AFEX reactor") 102 into which biomass, water and ammonia are introduced at an elevated pressure, i.e., about 100 to about 200 psi (6.8 to 13.6 atm), sufficient to maintain ammonia in liquid phase and moderate temperatures (which can be between about 25 and about 180° C. or higher, such as up to about 200° C.), thus exposing the biomass to concentrated ammonia. As such, a conventional AFEX process is not limited to the application of anhydrous ammonia, as some water is initially present with the biomass. Water can also be added to the biomass, as shown in FIG. 1, either prior to the biomass being provided to the reactor 102 or within the reactor 102, as shown, such that any anhydrous ammonia present is immediately converted into ammonium hydroxide.

Liquid ammonia flows to the bottom of the AFEX reactor 102 as a result of gravitational forces. Some amount of the liquid reacts with water and forms ammonium hydroxide. Depending on the thermodynamic gas-liquid state within the AFEX reactor 102, the remaining liquid can be converted to gaseous ammonia.

Residence time in the reactor 102 is directly correlated to the reaction temperature. For lower temperatures (i.e., between about 25 and 60° C., residence time can be on the order of hours to days. With higher temperatures (i.e., greater than about 100° C.), the residence time is on the order of minutes, such as between about 15 and about 60 min.

The reaction is terminated when a valve ($V_1$) is opened to release pressure from the AFEX reactor 102, which depressurizes (flashes) the pretreated biomass, vaporizes the ammonia, and terminates the AFEX reaction. The resulting ammonia gas, which passes through $V_1$, is then pressurized in a compressor 104, condensed in a first condenser 106 and recycled to the AFEX reactor 102 for reuse.

Recovery of ammonia for reuse is an objective when integrating a conventional AFEX system 100 into a broader biomass conversion process design. Additional ammonia can be recovered by separating ammonia still in contact with the pretreated biomass via evaporation in a dryer 108. In the embodiment shown in FIG. 1, the pretreated biomass is transferred to the dryer 108 to produce gaseous ammonia and dried pretreated biomass. The gaseous ammonia, which can also contain water, is condensed by a second condenser 110 and provided to an $NH_3$ column 112 for concentration. The dried pretreated biomass is transferred out of the dryer 108 for further processing.

Gaseous ammonia exiting the $NH_3$ column 112 is condensed in a third condenser 114, pumped up to pressure, and recycled to the AFEX reactor 102 to be reused in pretreating biomass. Water is removed from the $NH_3$ column 112 and condensed by a fourth condenser 116, and can join the dried pretreated biomass for further processing and/or be recycled into the bottom of the $NH_3$ column 112 for concentration.

While successful for ammonia recovery, the intensive drying and ammonia vapor compression steps of a conventional AFEX process are expensive. Additionally, if a suitable impeller is not included in the AFEX reactor 102, uneven mixing and pretreatment in the AFEX reactor 102 can occur. Mixing biomass (which contains solid slurries) with propellers and helical impellers is also energy intensive and may not be effective in reducing mass and heat transfer limitations. Only the biomass which is in contact with ammonium hydroxide and is suitably preheated (i.e., typically biomass close to the walls or at the bottom of the AFEX reactor 102) is likely effectively pretreated as compared to the bulk of the biomass in the AFEX reactor 102.

It can further be difficult to conduct conventional AFEX treatments in a continuous manner using pressurized liquid ammonia as the pretreatment chemical. The expansion release of ammonia at the end of a conventional AFEX pretreatment is energy intensive, generating gaseous ammonia-water mixtures that may cause the process to be commercially prohibitive.

Discussion of the Embodiments

In contrast, the various embodiments described herein allow ammonia to remain in effective contact with the biomass throughout the entire process, so as to reduce the total amount of ammonia utilized. The various embodiments described herein produce a biomass having high digestibility. In one embodiment, the water, ammonia and ammonia-water mixtures are added in an order and in a relative amount, at a temperature and concentration effective to produce high digestibility, i.e., providing more than about 80% glucan and xylan conversions within three days or less. In one embodiment, digestibility is greater than about 29% within three days or less.

In one embodiment, biomass is stored dry (such as less than about 10% moisture). Moist biomass is prepared by adding a desired amount of water and loading it into the reactor. In one embodiment, ammonia is then introduced into the reactor and contacts the moist biomass at a particular temperature and certain residence time. As will be described herein, in one embodiment, the ammonia is liquid ammonia. In one embodiment, gaseous ammonia is provided which condenses on the biomass. Once the reaction is complete, ammonia can be vented, with residual ammonia removed using carrier gas or steam.

The embodiments described herein include a method for treating biomass comprising delivering ammonia at an elevated temperature to a reactor; and allowing the ammonia to contact the biomass and react with water present in the biomass, wherein reactivity of polysaccharides in the biomass is increased as compared to polysaccharides in biomass which has not been pretreated. In one embodiment the ammonia is liquid ammonia and the method comprises an optimized ammonia fiber expansion (AFEX) pretreatment which includes a novel ammonia recovery process which does not include a drying step to dry pretreated biomass or an ammonia vapor compression step to recycle ammonia (optimized AFEX pretreatment). In one embodiment, the ammonia is gaseous ammonia which condenses on the biomass (GAP process).

Although one advantage of using ammonia during pretreatment is its relative ease of recovery and reusability due to its high volatility, until, now such recovery is very expensive. In an optimized AFEX system 200 utilizing an optimized AFEX process, however, recovery of ammonia is, for the first time, performed in an efficient and economical manner. In the embodiment shown in FIG. 2, the pretreated biomass exiting the AFEX reactor 102 is sent directly to the $NH_3$ column 112 to remove ammonia using high pressure steam. Thereafter, the pretreated biomass (containing a reduced amount of ammonia) is removed from the bottom of the $NH_3$ column 112 for further processing. Ammonia vapor exiting the top of the $NH_3$ column 112 passes through a first condenser 206 and a mixer 208 where additional water is added. Second and third condensers, 210 and 212, respectively, are used to cool the water and ammonia mixture. The cooled water and ammonia mixture then passes through a pump and a heater 214 which can be heated with high pressure steam before being recycled back into the AFEX reactor 102. As such, the efficient system 200 of FIG. 2 does not require an intensive drying step or ammonia vapor compression as is required in the conventional AFEX process shown in FIG. 1.

Any suitable mass ratio of lignocellulose biomass to ammonia can be used in the various embodiments. With the optimized AFEX system 200, the mass ratio of ammonia to biomass is between about 0.2 and 2 to 1, including any range there between, such as between about 0.3 and 0.5 to 1, such as no more than about 0.4 to 1 or no less than about 0.4 to 1. In one embodiment, the mass ratio is roughly between about 0.9 and 2 to 1. In one embodiment, the mass ratio is at least about 1 to 1 or no more than about 1 to 1.

Any suitable reaction temperature can be used in the optimized AFEX system 200. In one embodiment, the reaction temperature is between about 25 and about 180° C., including any range there between. In one embodiment, the temperature is between about 50 and about 150° C., including any range there between. In one embodiment, the temperature is between about 80 and about 100° C., including any range there between, such as, for example, between about 85 and 95° C., such as between about 89 and 91° C. In one embodiment, the temperature is at least about 90° C. or no more than about 90° C.

Figure 2:
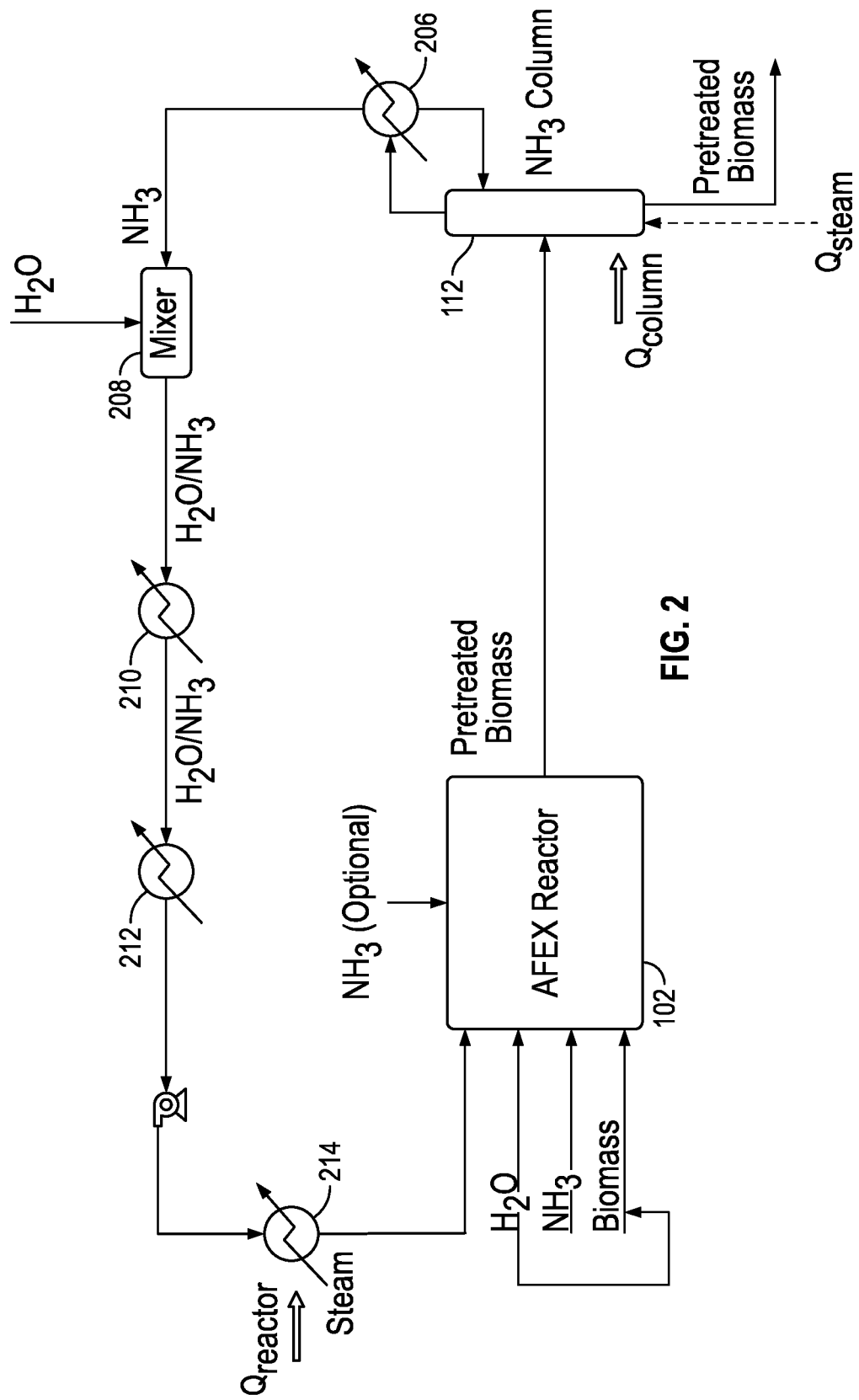
FIG. 2 is a process flow diagram for an optimized AFEX pretreatment according to an embodiment.

Generally speaking, the optimized AFEX system 200 of FIG. 2 utilizes a liquid bulk phase reaction through use of preheated liquid ammonia. The AFEX system 200 can also use mechanical mixing means (e.g., impellers) as otherwise, less than uniform mixing may occur, which can lead to use of additional ammonia. The AFEX system 200 can further use, in one embodiment, added water in the range of about 40 to about 100%. The optimized AFEX process can also be carried out on a continuous basis.

In one embodiment, pretreatment is accomplished with a fluidizing gas (rather than a liquid, i.e., liquefaction) in a gas bulk phase reaction. Use of gaseous ammonia can allow for more uniform mixing with fluidized gas rather than by mechanical means. The effective mixing with the gaseous ammonia also provides a highly efficient usage of ammonia and reduced amounts of water as compared to either a conventional or optimized AFEX process. Other benefits of a GAP process include, but are not limited to, negligible mass transfer issues, negligible heat transfer issues, low residence times, low ammonia/water usage, and avoidance of complex ammonia-water separation procedures.

Figure 3:
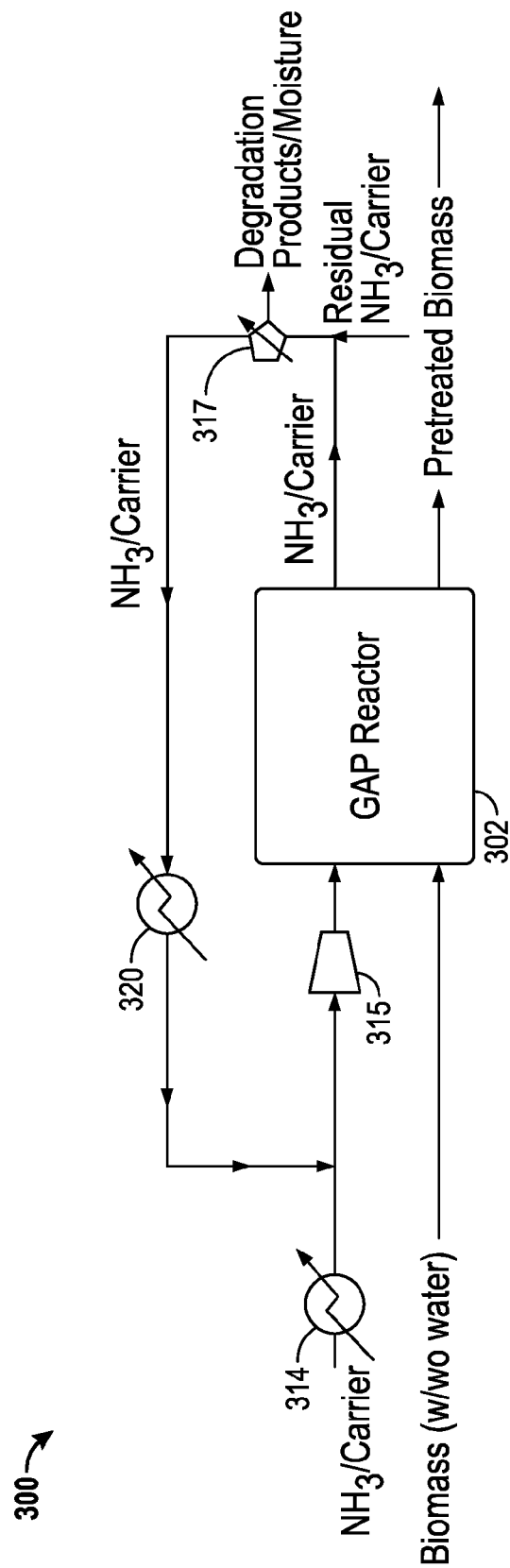
FIG. 3 is a process flow diagram for a gaseous ammonia pretreatment (GAP) according to an embodiment.

In the embodiment shown in FIG. 3, a "gaseous ammonia pretreatment" (GAP) system 300 is provided. In this embodiment, hot ammonia gas (i.e., gaseous ammonia) is used to pretreat biomass in a GAP reactor 302. In the embodiment shown in FIG. 3, biomass is added to the GAP reactor 302 with or without additional water. Ammonia and water are maintained in effective contact with the biomass during the pretreatment process. The GAP process, with its substantially homogenous heating, also provides better control over reaction kinetics.

Biomass inherently contains an amount of moisture or water, i.e., natural water. Typically, this natural water represents about 1% to about 20%, by weight, of the biomass, such as between about 5 and about 15% by weight, of the biomass. In general, this natural water tends to be bound in the biomass. As such, water can also be added to the biomass to increase the amount of moisture available to react. In one embodiment, the moisture content (MC) can be increased from the natural water content, of, for example, about 10% up to about 233%, dwb, including any range there between.

The addition of water with the ammonia during the pretreatment process results in two competing reactions; namely, hydrolysis (involving the hydroxyl ion) and ammonolysis (involving the ammonia). The degradation products formed due to hydroxyl ions are mostly acids which are potent inhibitors to microbes in downstream fermentation processes. On the other hand, the ammoniation reaction results in the formation of amides which are significantly less inhibitory to the microbes than their corresponding organic acids, as compared to either the conventional or optimized AFEX system. In one embodiment, about 0.5 to 2 kg water per kg of biomass is used in the GAP process. Because ammonia is soluble in water, it is expensive to distill out ammonia from water after the pretreatment in order to be reused in a continuous biorefinery process.

In one embodiment, biomass is fed to the reactor 302 continuously where it is pretreated substantially uniformly pretreated by the ammonia (i.e., the majority of the biomass receives about the same pretreatment) and requires short pretreatment times which vary depending on the temperature. A short pretreatment time also helps reduce formation of potentially inhibitory degradation products that might negatively influence downstream biological processing. In some embodiments, lower temperatures and longer pretreatment times are used. Further, with this method, there is no expansion release of pressure at the end of the pretreatment, allowing significant energy savings during recycling of the ammonia.

Depending on the temperature and pressure P1 of the hot ammonia gas fed to the reactor, the desired temperature in a GAP process is reached with a total residence time as low as 1 min, up to less than 15 min, including any range there between. In some embodiments, the residence time can be longer, such as up to about 120 min in the reactor, with a total residence time between about 1 min to about 120 min, although it is generally expected that the reaction time will be less than 15 min down to about 1 min, including any range there between.

For reaction temperatures close to room temperature (i.e., about 25 to about 40° C.) reaction times can be extended up to about 24 hours (depending on ammonia loading) for achieving close to 90% conversion. With temperatures in the range of about 98 to about 140° C., such as between about 99 and 101° C., such as about 100° C., the total residence time can decrease down to no more than about 15 min (depending on ammonia loading). In one embodiment, conditions in the reactor are about 50 to about 200° C., and about 0 to about 550 psig (0 to 37.45 atm) for a residence time of about 1 to about 120 min.

Any suitable mass ratio of lignocellulose biomass to ammonia can be used in the various embodiments. In one embodiment, biomass is impregnated with gaseous ammonia and water (using concentrated/dilute ammonium hydroxide) to achieve lower ammonia loadings (e.g., from about 0.01 to about 0.3 kg ammonia per kg biomass). With the GAP system 300, an effective biomass to ammonia loading can be from about 1:0.1 to about 1:5, such as from about 1:0.2 to about 1:2, or from about 1:0.2 (or 0.3) to about 1:1.

In one embodiment a carrier gas is used in combination with the ammonia, as shown in FIG. 3. An ammonia gas ($NH_3$)/carrier mixture (hereinafter "ammonia/carrier gas") can be heated with a first heater 314 and provided to a compressor 315 prior to being injected into the GAP reactor 302. Any suitable carrier (gas) can optionally be used together with the gaseous ammonia. In one embodiment, the carrier gas is either oxidative (e.g., oxygen or air) or non-oxidative (e.g., nitrogen or steam), and is either combined with gaseous ammonia before, during or after the pretreatment process (when removing residual ammonia from the biomass).

Most of the ammonia/carrier gas is recovered after completion of the pretreatment in the GAP reactor 302, condensed in a condenser 317 and reheated with a second heater 320 prior to being provided to the ammonia/carrier gas exiting the first heater 314 after the GAP process and preheated for the subsequent use in the pretreatment process. The residual moisture in the ammonia is removed using the condenser 317. The biomass volatiles (degradation products) and moisture along with the residual ammonia are also separated from the ammonia/carrier gas with the condenser 317.

As such, in one embodiment, there is continuous recycling of an ammonia-water-carrier gas mixture. In this way, the recycled mixture can be provided to the GAP reactor 302 to pretreat either pre-wetted biomass (e.g., about 10% up to about 233%, dwb, or substantially dry biomass (i.e., no more than about 15%, dwb).

In a GAP process, such as the embodiment shown in FIG. 3, the contents of the reactor may be maintained at pressures ranging from about 0 psi (0 atm) to about 1000 psi (68 atm), from about 200 psi (13.6 atm) to about 500 psi (34 atm), or from about 100 psi (6.8 atm) to about 200 psi (13.6 atm), including any range there between. In one embodiment, water is used to pre-wet the biomass, the hot ammonia/carrier gas is delivered to the biomass under pressure. For example, the hot ammonia/carrier gas can be delivered to the GAP reactor 302 at pressures ranging from about 0 psi (0 atm) to about 1000 psi (68 atm), from about 200 psi (13.6 atm) to about 500 psi (34 atm), or from about 100 psi (6.8 atm) to about 200 psi (13.6 atm). As noted above, the hot ammonia/carrier gas then condenses on the biomass and reacts with water present in the biomass and (optionally) added to the biomass.

In most embodiments, the desired temperature in the GAP reactor 302 is achieved substantially instantaneously due to an exothermic reaction between the water and ammonia in the hot ammonia gas stream. In one embodiment, the desired temperature is between about 25 and about 200° C., such as between about 25 and about 100° C. The formation of ammonium hydroxide takes place rapidly where ever water is associated with the biomass.

As such, the GAP process has many variables which can be adjusted, such as temperature of the gaseous ammonia before treatment, pressure P1 of the ammonia before delivery, pressure P2 of the ammonia after delivery, reaction time in the GAP reactor, water content of the biomass, and ammonia loading impact. Set-point temperature can also be achieved much more quickly with an increase in pressure, since hot gaseous ammonia also carries heat through the bulk phase to the interior of the biomass, where the reaction is primarily occurring.

In one embodiment, only a small portion of ammonia (about 0.5 to about 3%, w/w of ammonia/biomass) is reacted during the GAP process (due to reaction of ammonia with various cell wall components) and the remaining ammonia (i.e., from about 50% to about 98%, from about 75% to about 98%, or from about 90% to about 98%, w/w of ammonia/biomass) can be recycled in its gaseous state.

In addition to gaseous ammonia pressure and temperature, particle size of the biomass can also affect the reaction time. Any suitable size and shape of particle can be used. With a smaller the particle size, however, it is expected that the set-point temperature and pressure in the interior of the particle will be achieved more quickly, which means that complete conversion should be completed in a shorter time period. In one embodiment, the particles are elongated in one dimension. In one embodiment, the particles have at least one dimension no greater than about 10 cm and no less than about 0.1 cm, such as at least about 0.5 cm. The diffusion rate of ammonia through a biomass particle increases with increasing pressure, such that the reactant can access the reactive bonds much more quickly and reduce the total reaction time as compared with conventional processes. In theory, if gaseous ammonia pressure is doubled, the reaction time may decrease by nearly 50%, since most reactions in the biomass are pseudo-first order.

As with the optimized AFEX system shown in FIG. 2, the GAP system 300 can be easily adapted to a continuous method in which the GAP reactor 302 is continuously fed with a stream of recycled ammonia gas, a mixture of recycled ammonia gas and steam, recycled ammonia gas combined with an inert or other carrier gas, or a recycled ammonia/steam gas mixture combined with an inert/carrier gas in any of a fluidized bed reactor, a semi-fluidized bed reactor, or a fixed bed reactor. In this way, the biomass is contacted with hot ammonia and/or an inert carrier gas.

Figure 4B:
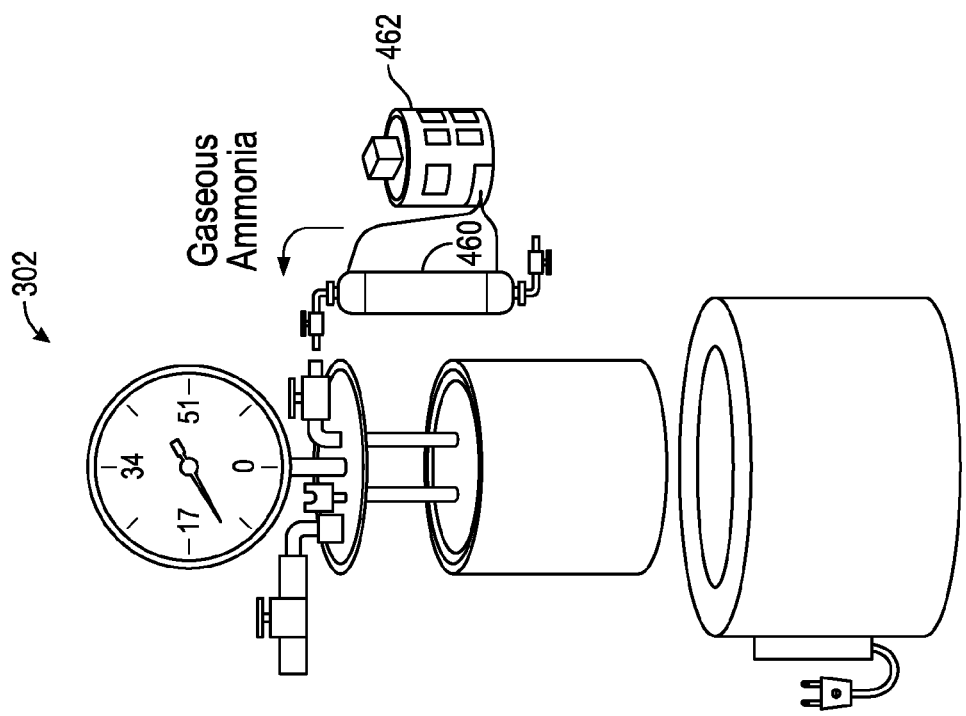
FIGS. 4A and 4B shows a comparison of an AFEX process (FIG. 4A) and the GAP process of FIG. 3 (FIG. 4B) according to various embodiments.
Figure 4A:
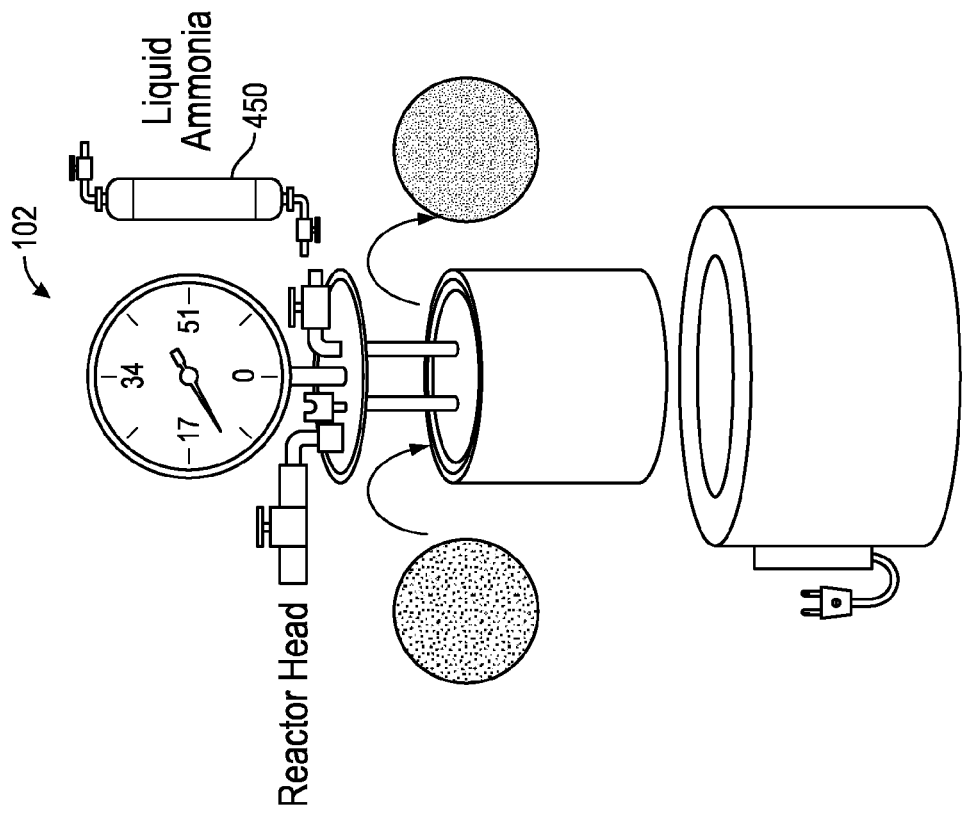

FIGS. 4A and 4B are schematic illustrations of an AFEX reactor 102 (FIG. 4A) (for either a conventional or optimized AFEX process) and a GAP reactor 302 (FIG. 4B). In the AFEX reactor 102 shown in FIG. 4A, liquid ammonia is delivered to the AFEX reactor 102 under pressure through a bottom valve of an AFEX ammonia delivery vessel 450. In the GAP reactor 302 shown in FIG. 4B, gaseous ammonia is delivered to the GAP reactor 302 under pressure through a top valve of a GAP ammonia delivery vessel 460.

With respect to the optimized AFEX process carried out in the AFEX reactor 102 of FIG. 4A, concentrated ammonium hydroxide under pressure is used to improve the accessibility/digestibility of the monosaccharide moieties from biomass. In some embodiments, combinations of anhydrous ammonia and concentrated ammonium hydroxide solutions are used to obtain results that not obtainable by either dilute ammonium hydroxide or anhydrous ammonia acting alone. As such, various embodiments are provided to minimize the amount of ammonia in the gas phase so that a maximum amount of ammonia is in the liquid phase and available to react with the biomass, either as ammonium hydroxide or liquid ammonia. In one embodiment, the lignocellulosic material is treated with concentrated ammonium hydroxide in an amount greater than 30% by weight in an ammonium hydroxide solution.

The gaseous ammonia in FIG. 4B is produced when liquid ammonia in the ammonia delivery vessel 460 is heated with a heater 462 to its gaseous state (at pressure P1). The gaseous ammonia is delivered to the GAP reactor 302, such that the final pressure in the GAP reactor 302 is P2. The pretreatment conditions, such as temperature of the gaseous ammonia before treatment, pressure P1 of the ammonia before delivery, pressure P2 of the ammonia after delivery, reaction time in the GAP reactor, water content of the biomass, and ammonia loading impact the GAP process.

Delivery of heated gaseous ammonia in this manner allows the hot ammonia gas to condense on the biomass, thereby causing a fast (e.g., instantaneous) rise in temperature in the GAP reactor 302. In comparison, it typically takes about 15 to about 45 min to reach the desired pretreatment temperature in the AFEX reactor 102 of FIG. 4A, after which the temperature is maintained for a residence time sufficient to complete the reaction at that temperature.

Figure 5:
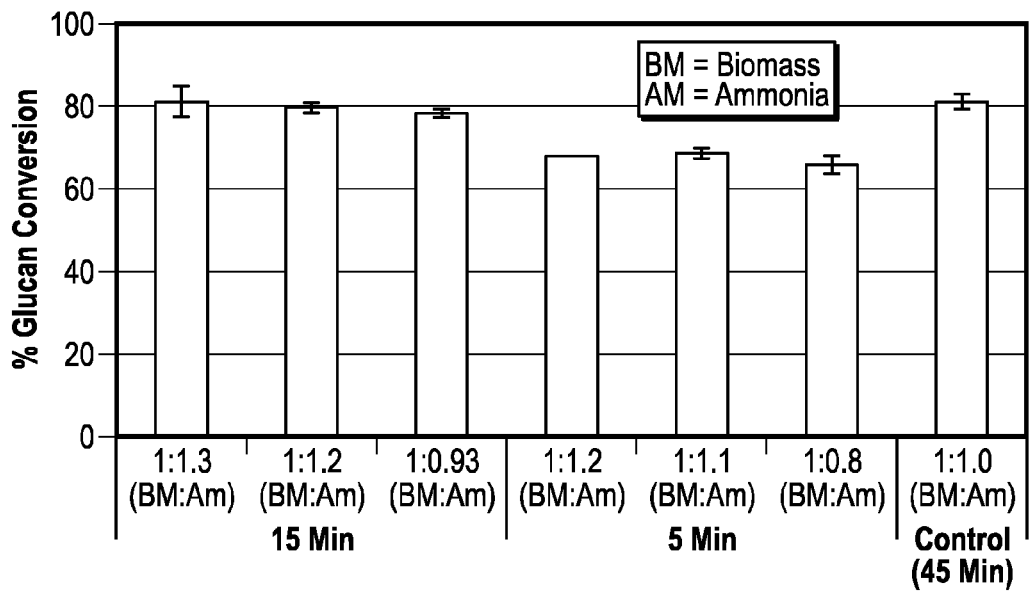
FIG. 5 shows enzymatic hydrolysis based glucose yield from corn stover pretreated using a conventional or optimized AFEX (control) process and GAP process at two different residence times as a function of ammonia loading according to various embodiments.

In one embodiment, glucan conversion rates in a GAP process are the same, or higher (by about 10 to about 15%) than conversion rates for either conventional or optimized AFEX. For example, as shown in FIG. 5 (discussed in Example 38), a 15 minute reaction time with a GAP process achieves a relatively equivalent conversion rate as a 45 minute reaction time with either a conventional or optimized AFEX process. With a 30 minute reaction time with GAP, however, it is expected that the glucan conversion is increased by about 10 to about 15% as compared to either the conventional or optimized AFEX process. Generally, such conversion rates are dependent on other factors, such as, the particular cellulases and hemicellulases, the type and combination of enzymes, and the amount of enzymes used in the enzymatic hydrolysis.

Figure 6:
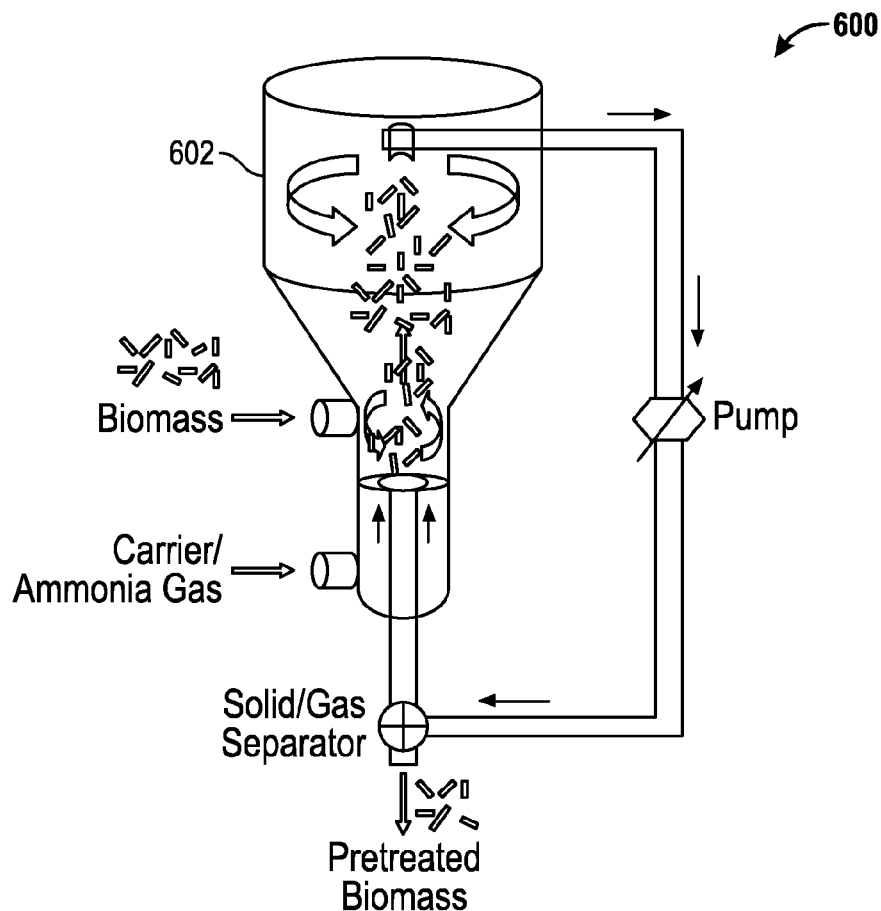
FIG. 6 shows fluidization during a GAP process using gaseous ammonia with or without suitable hot carrier gases according to various embodiments.

FIG. 6 shows a continuous GAP system 600 in which the GAP process is carried out by fluidizing the biomass using gaseous ammonia and one or more inert gases (as carrier gases). The fluidized-based treatment provides uniform pretreatment conditions and is relatively easy to scale up as a continuous process, to include recycling and reusing of hot gaseous ammonia. In this embodiment, the batch GAP reactor 602 contains a fixed bed of biomass which is continuously purged with hot ammonia and/or inert gas. In the embodiment shown in FIG. 6, the hot gas is recovered and recycled back into the GAP reactor 602.

Figure 7:
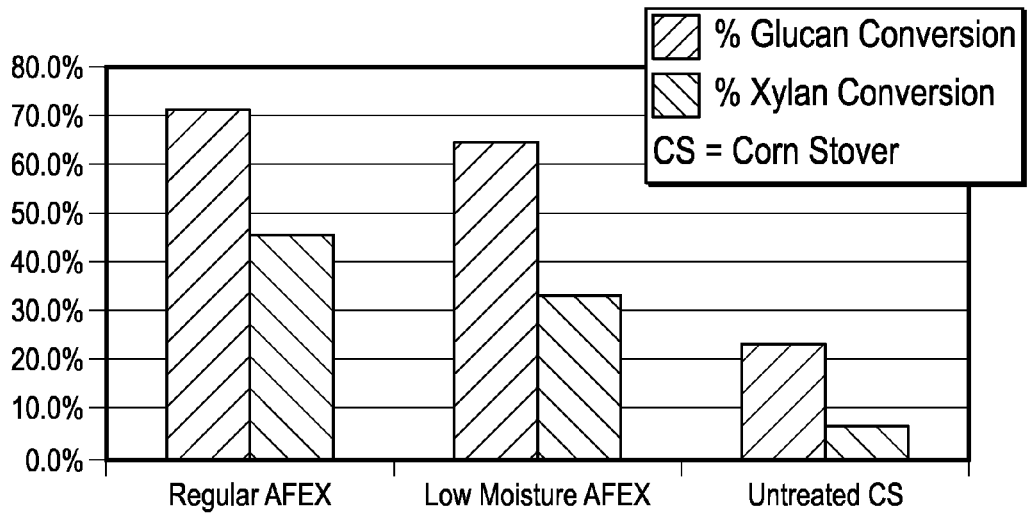
FIG. 7 shows glucose yield for untreated, high moisture (60%, dwb) and low moisture (5%, dwb) conventional AFEX treated corn stover according to various embodiments.

Using the GAP process, it is expected that biomass containing from about 5 to about 15% moisture, dwb (typical moisture content of field dried biomass without external water supplementation during pretreatment), can be pretreated with hot ammonia gas. In other embodiments, the biomass is pre-wetted to add moisture. The percent glucan conversion is similar to that obtained from high moisture (15% or more, dwb) ammonia pretreatment as shown in FIG. 7.

In various embodiments, means for maintaining ammonia and water in contact with the heated mixture is provided by minimizing or otherwise managing the headspace (vapor phase) of the reactor containing heated biomass, ammonia and water. In one embodiment, the ammonia is compressed by a mechanical means for reducing the volume of a headspace inside the closed vessel and thereby increasing a fraction of the total ammonia that is in the liquid phase. In one embodiment, the carrier gas serves this purpose, by increasing a fraction of the total ammonia that is in the liquid phase. By maintaining pressure (via the carrier gas) on the headspace of the reactor, the amount of ammonia required to obtain a desired glucose yield can be reduced. Carrier gas overpressure minimizes the amount of ammonia that evaporates from the biomass and keeps more ammonia in contact with the biomass, thereby increasing treatment effectiveness. In one embodiment, particles of an inert solid material, such as iron filings, are introduced into the vessel so as to increase a fraction of the total ammonia that is in the liquid phase.

The processes described herein further do not degrade biomass carbohydrates and compromise yield. In one embodiment, high overall yields of glucose (nearly 100% of theoretical) and 85% of theoretical yields of xylose, are obtained. In one embodiment, low application rates of expensive hydrolytic enzymes are used. Additionally, in one embodiment residual ammonia can serve as a nitrogen source for subsequent fermentations or animal feeding operation. In one embodiment, treated biomass and polysaccharides can be fed at very high solids levels to subsequent process operations, thereby increasing the concentration of all products and reducing the expense of producing other chemicals from the polysaccharides. Furthermore, by using different ammonia and ammonium hydroxide combinations, in combination with different water levels in the biomass, in one embodiment, the process can be easily retrofitted into existing ammonia recovery operations, thus minimizing costs and maximizing treatment effectiveness. The reactor headspace can, in one embodiment, be managed to minimize ammonia evaporation into the gas phase, thus further improving process economics by minimizing the amount of ammonia required to achieve an effective treatment.

A number of markets may benefit from the various embodiments described herein, including, but not limited to, the chemical and biofuel industry, the fermentation industry and the animal feed industry. In one embodiment, the GAP process is used in a lignocellulosic biorefinery for producing biofuels and biochemical, with a reduction in greenhouse gas (GHG) emissions, as well as a reduction in pretreatment and processing costs.

In one embodiment, the GAP process is used in the edible oilseed and oilcake industry. Oilseeds are typically extracted in two stages, namely mechanical expeller/press extraction for reducing oil content to 20-25% (w/w), followed by hexane extraction to remove residual oil. The extracted oilcake is then toasted (or desolventized) by steam stripping/cooking to remove residual solvent and pre-conditioned (i.e. to detoxify anti-nutritional components in the oilseed) for animal consumption and/or protein extraction. The pre-conditioning process is generally dependent on the type of oilseed, but typically requires cooking the biomass (at suitable moisture content) with steam at about 90 to about 110° C. for a period of about 15 to about 30 min.

In one embodiment, the GAP process is used in combination with a conventional steam toasting process to pretreat the biomass prior to subsequent biological processing for producing biofuels and chemicals (e.g. ethanol and biodiesel). In one embodiment, the fiber portion of the oilcake is fermented to ethanol and reacted with the oil extracted from the oilseed to produce biodiesel as well. In one embodiment, a GAP pretreatment process is used to pretreat oilseed cakes for biomass conversion applications. In one embodiment, GAP is used for protein extraction as animal feed. In the "PRO-XAN process" proteins are extracted from alfalfa through hammer milling to disrupt cell walls followed by juice extraction from screw press and steam injection to coagulate proteins. See, for example, Prevot-D'Alvise N, et al., "Development of a pilot process for the production of alfalfa peptide isolate," Chem. Technol. Biotechnol. 78:518-528 (2003). Solubles are added to press cake and sold as animal feed. In this process, ammonia is used to kill different microbes and to raise the pH, which also helps to extract protein.

The invention will be further described by reference to the following examples, which are offered to further illustrate various embodiments of the present invention. It should be understood, however, that many variations and modifications may be made while remaining within the scope of the present invention.

Examples 1-20

Conversion of Corn Stover to Glucose and Xylose Following Treatment with Ammonia and Water Experimental Procedure and Results This testing was directed to an optimized AFEX process which includes the improved ammonia recovery as described above and shown, in one embodiment, in FIG. 2.

Kramer corn stover having a moisture content of about 15% dry weight basis (dwb) was ground with a Whiley knife mill to about 0.5 cm in dimension or diameter. The ground corn stover (hereinafter "biomass") was then added to a 300 ml reactor vessel (e.g., 102, hereinafter "reactor"), i.e., PARR unit with pressure and temperature monitoring attachments, and wetted to the desired moisture level (Table 1). The reactor vessel was then sealed.

Hot ammonium hydroxide/water solutions were added to the biomass in the reactor in an amount sufficient to increase the temperature inside the reactor to 50° C. The intermediate ammonia to dry biomass mass ratio was about 0.2 to 1 while water to dry biomass mass ratio was about 0.4 to 1. Sufficient time, i.e., about 5 min, was allowed for the reaction to occur under these conditions. The pretreated biomass was then compressed with a screw reactor to minimize the volume of vapor or "dead" space according to the method described in, Sendich, E. N., et al., "Recent process improvements for the ammonia fiber expansion (AFEX) process and resulting reductions in minimum ethanol selling price," *Bioresource Technology*, 99, 8429-8435 (2008), (hereinafter "Sendich").

With respect to the hot ammonium hydroxide/water solutions, a concentrated ammonium hydroxide mixture was prepared by mixing the desired proportions of anhydrous ammonia at temperatures as specified in Sendich. This mixture was added to the biomass in the 300 ml reactor vessel in an amount sufficient to achieve the desired final level of ammonia and water, namely 1 kg of ammonia per kg of dry biomass and 0.6 kg of water per kg of dry biomass. The mixture of ammonia, water and biomass was heated to 90° C., held at that temperature for about 5 min, after which the pressure was rapidly released. The resulting solid was hydrolyzed to mixtures of monosaccharide moieties containing, for example, glucose, xylose and arabinose. The tendency of ammonia to convert to gas was further reduced by pressurizing the system with nitrogen and by mixing steal beads with the biomass.

Essentially anhydrous liquid ammonia was then added to the intermediate mixture to obtain a final ammonia level of about 0.5 kg ammonia (as $NH_3$) per kg of dry biomass and temperatures of about 90° C. The new mixture was held at these conditions for an additional 5 min and the pressure was rapidly released to remove and recover the ammonia. The resulting solids were hydrolyzed to mixtures of simple sugars containing glucose, xylose and arabinose.

Table 1 shows the results for the conversion of corn stover to glucose and xylose following treatment of biomass with varying amounts of ammonia and water under varying conditions. More specifically, Table 1 shows the results of enzymatic hydrolysis of biomass treated with ammonia, water and heat under the same final conditions of 1 kg of ammonia per 1 kg of corn stover biomass (dry weight) and 0.6 kg of water per kg of corn stover biomass (dry weight) at a final reaction temperature of 90° C. These final conditions were chosen to reproduce the optimal pretreatment conditions demonstrated for "conventional" (using anhydrous ammonia) AFEX treatment of corn stover. The first row of results shows the glucose and xylose yields (93% and 75%, respectively) obtained under these "conventional" AFEX pretreatment conditions.

Each "Expt. #" is considered a separate example. The total amount of water, ammonia and corn stover and the system temperature was the same for all experiments. The corn stover was treated with 1 kg of ammonia per 1 kg dry corn stover. The experiments were run at 90° C. with a five minute holding time. The treated corn stover of "Expt. 1" was hydrolyzed with 15 filter paper units of cellulose per gram of cellulose in the corn stover. As such, the final conditions to which the corn stover was subjected were substantially identical for each experiment. However, the way in which these final conditions were reached varied significantly, producing novel and surprising results.

TABLE 1

Experimental Set-up and Results
Glucose and Xylose yields of ammonia treated corn stover after 168 hr (7 days) for hydrolysis with a cellulose enzyme. Different ammonia concentrations were used. All runs are at 1 kg NH3:1 Kg dry stover (BM), 90° C., reactor temperature, 0.6 kg water/kg dry stover (except for the last 4 experiments 17 to 20) and 5 min residence time. 15 FPU cellulase enzyme/gram glucan in BM.

| Expt. # | Kg $NH_3$/kg water in ammonium hydroxide | Ammonia distribution | Water distribution | % Glucose yield | % Xylose yield | Repeats |
|---|---|---|---|---|---|---|
| 1(a) | 1 | All $NH_3$ | All in BM | 92.96 | 74.25 | 2 |
| 2 | 0.5 | ¾ $NH_3$ and ¼ $NH_4OH$ | ½ in $NH_4OH$ ½ in BM | 92.20 | 78.85 | 2 |
| 3 | 0.5 | ¾ $NH_3$ and ¼ $NH_4OH$ | All in $NH_4OH$ | 79.88 | 64.90 | 2 |
| 4 | 0.41 | ⅔ $NH_3$ and ⅓ $NH_4OH$ | All in $NH_4OH$ | 86.60 | 70.54 | 1 |
| 5 | 0.58 | ⅔ $NH_3$ and ⅓ $NH_4OH$ | ½ in $NH_4OH$ ½ in BM | 78.23 | 65.83 | 1 |

TABLE 1-continued

Experimental Set-up and Results
Glucose and Xylose yields of ammonia treated corn stover after 168 hr (7 days)
for hydrolysis with a cellulose enzyme. Different ammonia concentrations were
used. All runs are at 1 kg NH3:1 Kg dry stover (BM), 90° C., reactor
temperature, 0.6 kg water/kg dry stover (except for the last 4 experiments
17 to 20) and 5 min residence time. 15 FPU cellulase enzyme/gram glucan in BM.

| Expt. # | Kg $NH_3$/kg water in ammonium hydroxide | Ammonia distribution | Water distribution | % Glucose yield | % Xylose yield | Repeats |
|---|---|---|---|---|---|---|
| 6 | 0.5 | ½ $NH_3$ and ½ $NH_4OH$ | All in $NH_4OH$ | 57.65 | 47.85 | 1 |
| 7 | 0.8 | ½ $NH_3$ and ½ $NH_4OH$ | ¾ in NH4OH and ¼ in BM | 85.50 | 70.37 | 1 |
| 8 | 0.66 | ½ $NH_3$ and ½ $NH_4OH$ | ½ in $NH_4OH$ ½ in BM | 97.78 | 81.98 | 2 |
| 9 | 0.79 | ½ $NH_3$ and ½ $NH_4OH$ | ¾ in BM and ¼ in $NH_4OH$ | 98.54 | 78.70 | 2 |
| 10 | 0.38 | ⅓ $NH_3$ and ⅔ $NH_4OH$ | All in $NH_4OH$ | 74.52 | 56.47 | 1 |
| 11 | 0.73 | ⅓ $NH_3$ and ⅔ $NH_4OH$ | ½ in $NH_4OH$ ½ in BM | 81.51 | 69.66 | 1 |
| 12 | 0.66 | All $NH_4OH$ | All in $NH_4OH$ | 71.00 | 57.00 | 2 |
| 13 | 0.75 | All $NH_4OH$ | ½ in $NH_4OH$ ½ in BM | 96.78 | 79.00 | 3 |
| 14 | 0.88 | All $NH_4OH$ | ¾ in $NH_4OH$ and ¼ in BM | 97.11 | 79.00 | 2 |
| 15 | 0.72 | All $NH_4OH$ | ¼ in $NH_4OH$ and ¾ in BM | 88.31 | 75.37 | 2 |
| 16(b) | 0.3 | All $NH_4OH$ | 2.3 g water per g BM | 83.58 | 68.18 | 1 |
| 17(b) | 0.15 | All $NH_4OH$ | 5.6 g water per g BM | 70.50 | 42.46 | 1 |
| 18(b) | 0.1 | All $NH_4OH$ | 9 g water per g BM | 64.85 | 49.31 | 1 |
| 19(b) | 0.05 | All $NH_4OH$ | 19 g water per g BM | 51.26 | 39.32 | 1 |
| 20(c) | Control | No ammonia | Not applicable | 29.5 | 17.5 | 2 |

Note:
Pressures range from about 100 psi to about 300 psi except for Expt. 16-19, which are at atmospheric pressure
(a)Comparative Example 1 shows the AFEX process described in U.S. Pat. Nos. 4,600,590 and 5,037,663 to Dale, exemplified by FIG. 1.
Comparative Examples 16 to 19(b) show the results at atmospheric pressure with ammonium hydroxide.
Example 20(c) shows the process without ammonia.

The column entitled "Ammonia Distribution" contains information on whether the ammonia (as $NH_3$) was added as anhydrous ammonia or as ammonium hydroxide (ammonia in water). For example, "all $NH_3$" refers to addition of ammonia as anhydrous liquid ammonia directly from the pressure tank. The phrase "ALL $NH_4OH$" refers to addition of ammonia as aqueous ammonium hydroxide.

The column entitled "Water Distribution" contains information on whether the water was added to the corn stover directly or added as part of the ammonium hydroxide. For "Expt. 1a" ("conventional AFEX"), the terms "all $NH_3$" and "All of the water in BM" refer to conditions in which all the ammonia was added as anhydrous and all of the water was in the biomass, respectively. Experiments 16-19(b) were performed with ammonia added as ammonium hydroxide, with water added either to the stover or with the ammonium hydroxide, i.e., "All $NH_4OH$." These experiments were performed at essentially ambient pressure treatments of biomass by ammonia, as compared to the concentrated ammonia systems at higher than ambient pressure conditions of Experiments 1-15.

Final glucose yield, and to a lesser extent, xylose yield, following enzymatic hydrolysis are key determinants of process economics for biomass conversion systems. If 90% yield of glucose is somewhat arbitrarily chosen as the target economic yield, then it becomes obvious that only a fraction of all of the possible means for reaching the desired final conditions of 1:1 ammonia to biomass and 0.6:1 water to biomass are in fact effective in achieving this target yield. For example, from Table 1, experiments #6 and #9 differ only in the amount of water that is added to the system via biomass or via ammonium hydroxide, and yet the differences in enzymatic hydrolysis yields are quite large, i.e., 58% vs. 99%, respectively. These results are unexpected and surprising. It is not apparent why combining ammonia, water and biomass in different initial proportions but the same final proportions, should achieve such different results.

Thus, depending on how the ammonia and water are added, very different results were obtained. Using the criteria that 85% conversion of cellulose to glucose is a minimum for cost competitive process, Table 1 shows the % yield after 168 hours of hydrolysis for both glucose and xylose. When water was added as ammonium hydroxide (comparatively more dilute ammonium hydroxide) the 85% criterion was not achieved for glucose.

Examples 21 to 36

AFEX Treatment of Corn Stover Under Nitrogen Pressure

This series of experiments was performed to verify that it is ammonia in the liquid phase which causes the updated AFEX process to be more efficient by allowing direct contact with the biomass. In this testing ammonia evaporation was minimized by applying nitrogen pressure during pretreatment of the biomass. Ammonia loading under nitrogen was also optimized.

Experimental Procedure and Equipment

Kramer stover with 36.1% glucan content was received from the National Renewable Energy Laboratory (NREL, Golden, Colo.). The moisture content of the biomass was adjusted from 10% to the desired level before placing in the reactor. The reactor was a 300 ml PARR unit with pressure and temperature monitoring attachments. The sample in the reactor was topped off with spherical steel balls to reduce the void in the reactor and to have similar conditions with experiments without use of nitrogen.

A predetermined amount of anhydrous ammonia was charged in a reactor using a sample cylinder. Nitrogen gas was introduced to the reactor from a nitrogen cylinder tank via a pressure regulator. The reactor was gradually heated up by a heating mantle until it reached 90° C. After 5 min of residence time, the reactor was rapidly depressurized. Both temperature and pressure were recorded every 2 min during the experiments. The pressure started at about 400 psig (27.2 atm) and ended at about 750 psig (51 atm) while the reactor temperature started from about 50° C. to 90° C. where it was vented.

A Waters High Performance Liquid Chromatography (HPLC) with Aminex HPX 87 P BioRad Column and de-ashing guard column was used to perform the analysis.

Experimental Conditions

Figure 8:
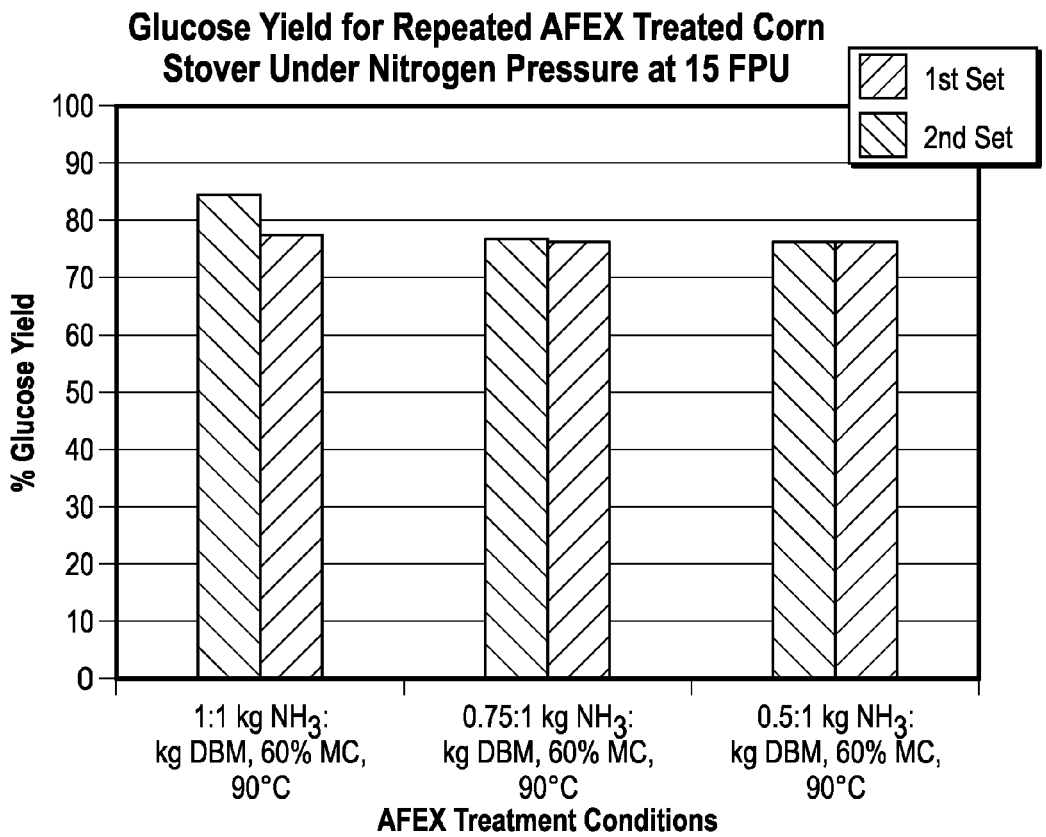
FIGS. 8 and 9 are graphs showing two separate AFEX treated corn stover experiments under nitrogen pressure with the same treatment conditions, and with no ammonia recovery, according to various embodiments.
Figure 9:
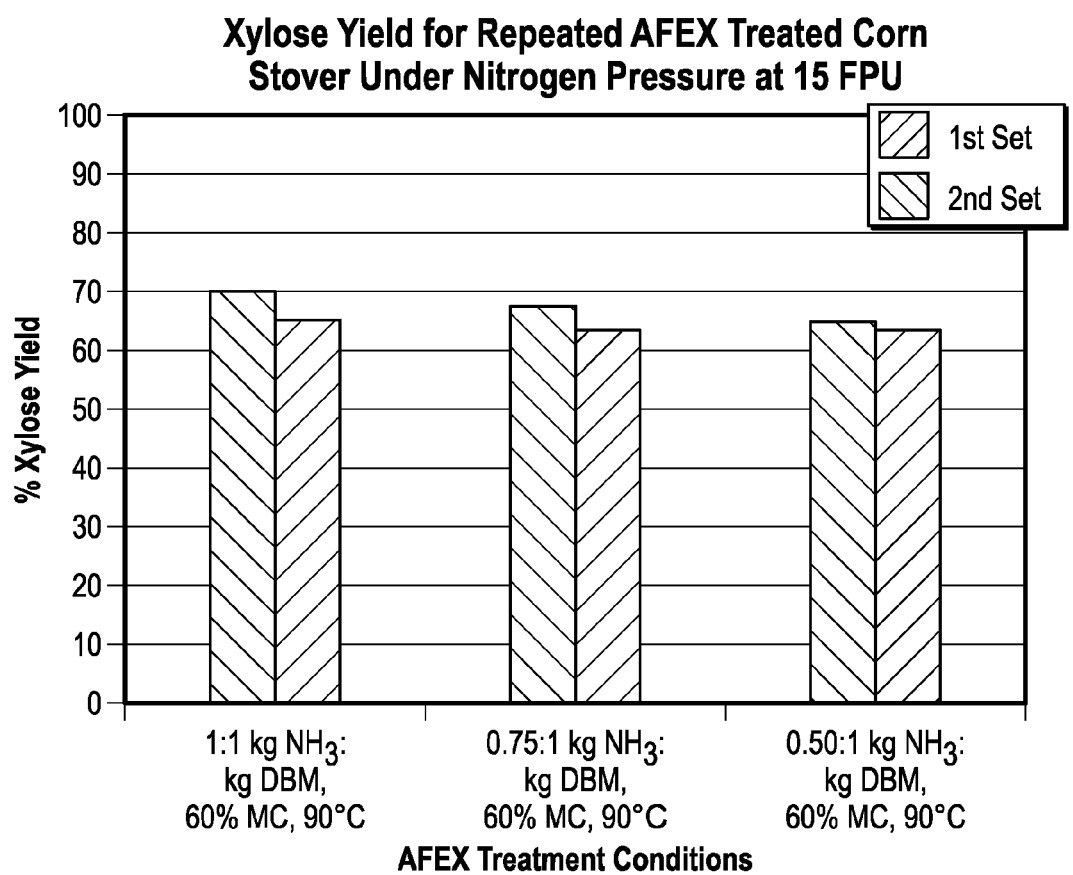

For Experiments 21 to 24, the previous optimal conditions of biomass (60%, dwb) moisture content, 90° C. treatment temperature and 5 min residence time were chosen, although the amount of charged ammonia was varied to determine optimal ammonia loading under $N_2$ pressure. (FIGS. 8 and 9).

In the second set of Experiments, 25 to 30, varying moisture content (FIGS. 10 and 11) and varying ammonia (FIGS. 12 and 13) loadings were used.

Figure 14:
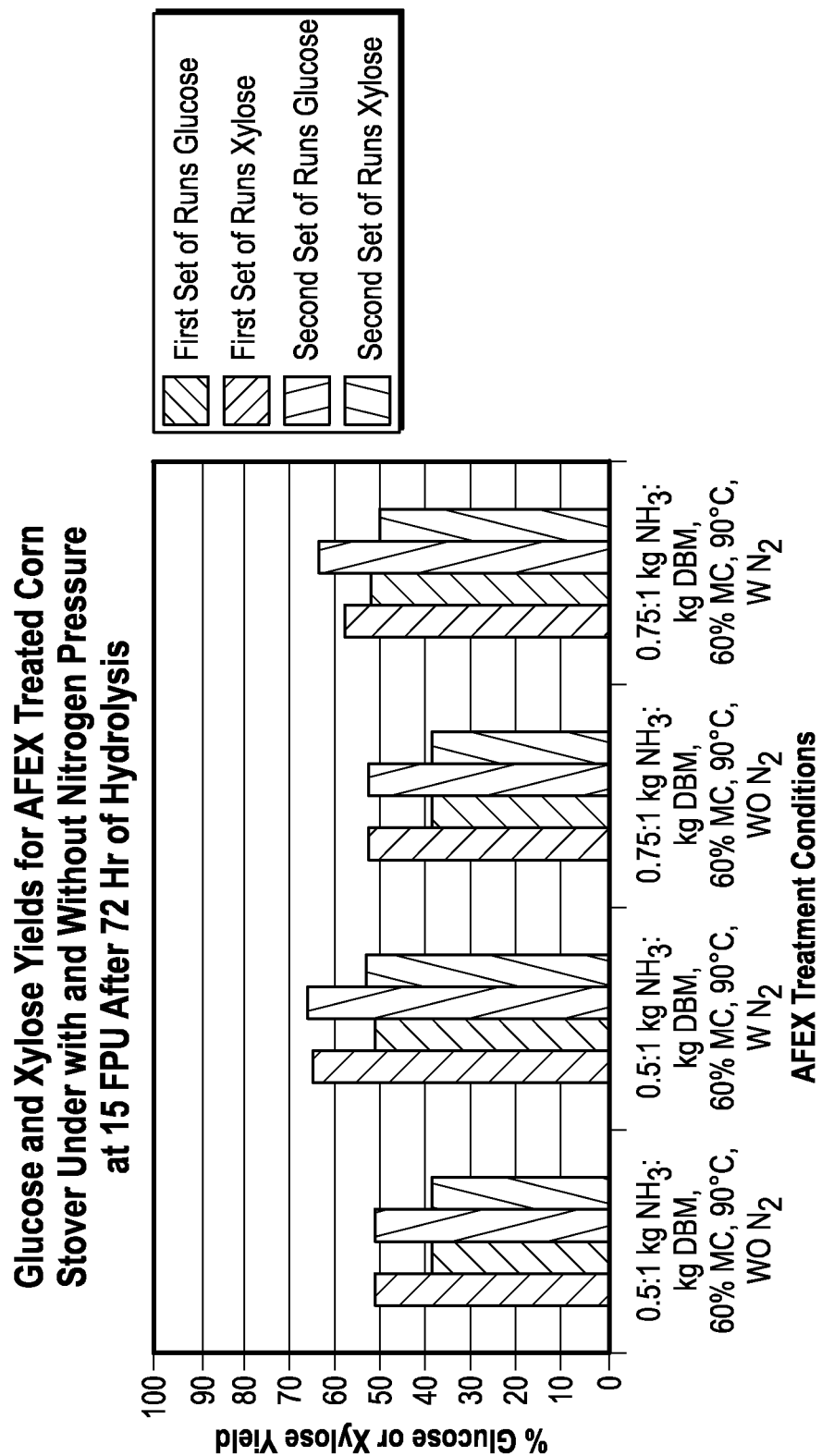
FIG. 14 is a graph showing the overall glucose and xylose yields of two separate sets of conventional AFEX treated corn stover treatments under nitrogen pressure, which are repeated, according to various embodiments.
Figure 15:
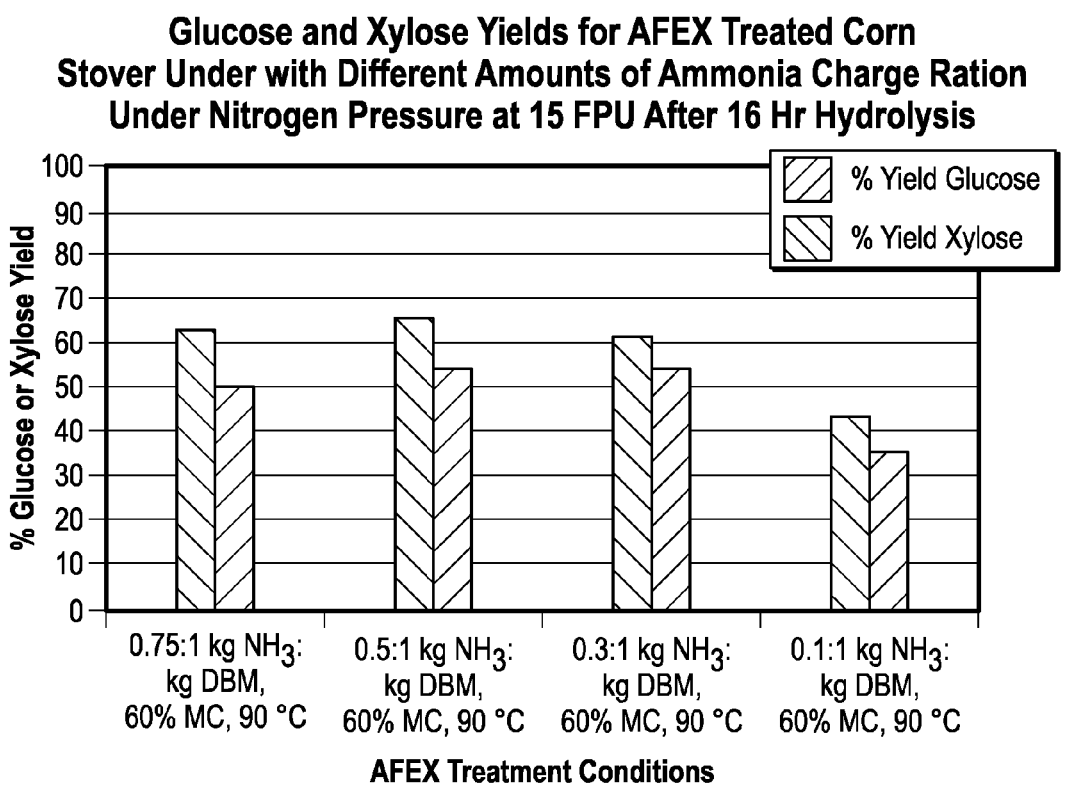
FIG. 15 is a graph showing a yield trend as the kg amount of ammonia per unit kg of dry biomass (DBM) is decreased according to various embodiments.

In the third set of Experiments, 31-36, a conventional AFEX test was run. (FIGS. 14-16).

Hydrolysis

For hydrolysis, NREL Lap-009 Protocol was followed. Duplicate samples were prepared and hydrolyzed for a period of 168 hr. At time intervals of 24 hr, 72 hr and 168 hr, samples were taken for HPLC analysis. To all samples were added 15 FPU per g of glucan of Spezyme CP (CAFI 1), Old enzyme with 28.2 FPU/ml.

Analysis

In the optimized AFEX pretreatment conditions of 1 kg $NH_3$:1 kg DBM, 60% MC, 90° C. ideally, there is 90% glucose and 70% xylose conversion. If the decrease in the amount of ammonia used under nitrogen pressure is back calculated, there is a 1.5, 2 and 5 fold increase in yield under nitrogen pressure proportional to the ammonia loadings of 0.5, 0.3 and 0.1 kg $NH_3$:Kg DBM, respectively. In other words, there is a 5-fold reduction in the amount of ammonia being used when AFEX under nitrogen pressure is employed at 0.1:1 ammonia charge, as compared to a ratio of 1:1. The amount of ammonia decreased about 10 times, from 1:1 to 0.1:1, while both the glucose and xylose yields dropped by ½, from about 90% to about 45% and about 70% to about 35% for glucose and xylose, respectively.

FIGS. 8 and 9 show results of two separate AFEX treated corn stover experiments under nitrogen pressure with the same treatment conditions.

Figure 10:
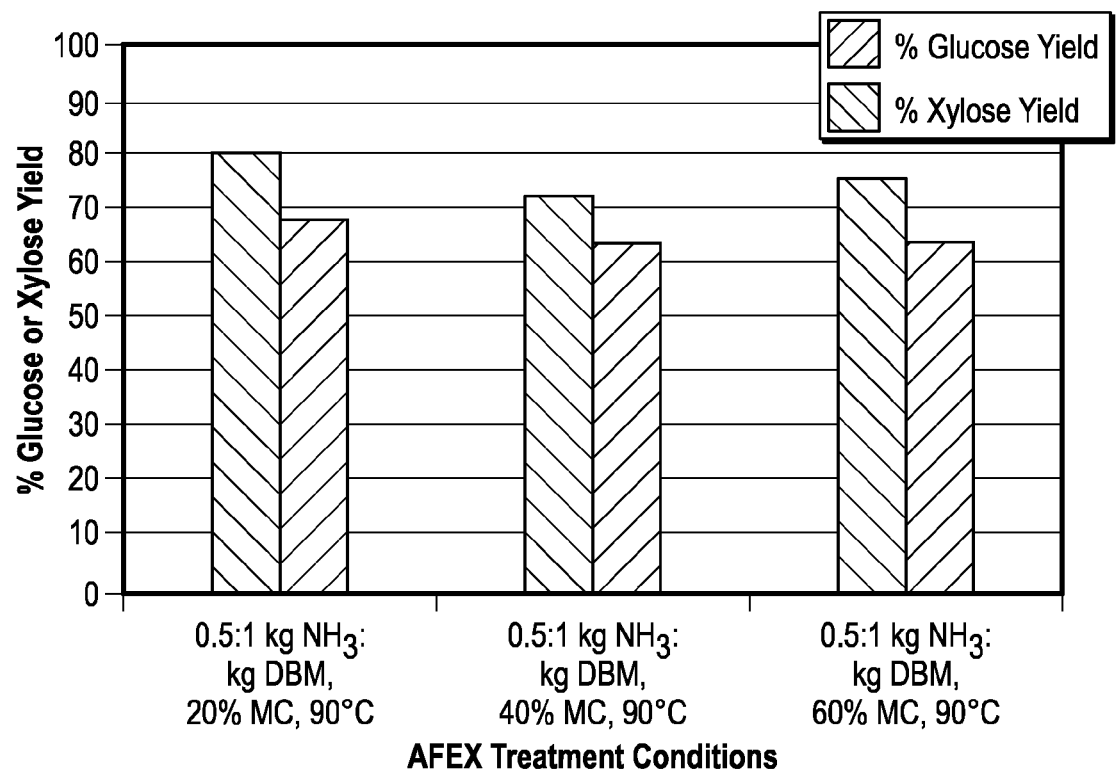
FIG. 10 is a graph showing differences in yield as a result of differences in moisture content according to various embodiments.
Figure 11:
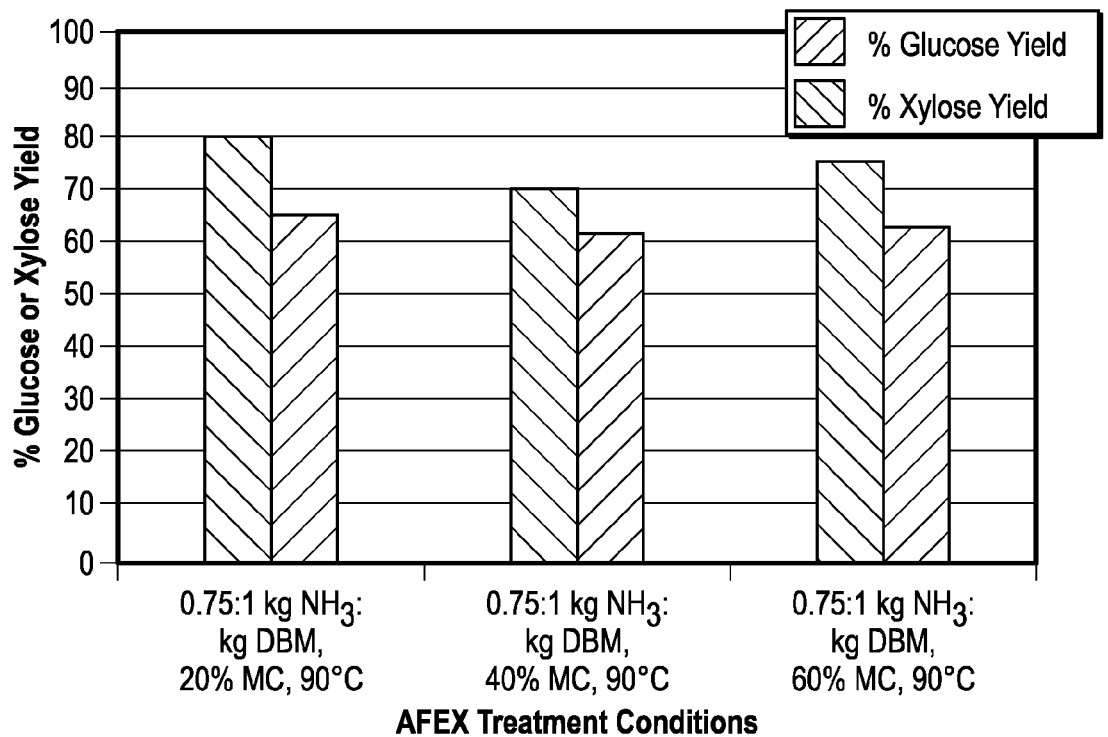
FIG. 11 is a graph showing differences in yield as a result of differences in ammonia loadings according to various embodiments.
Figure 12:
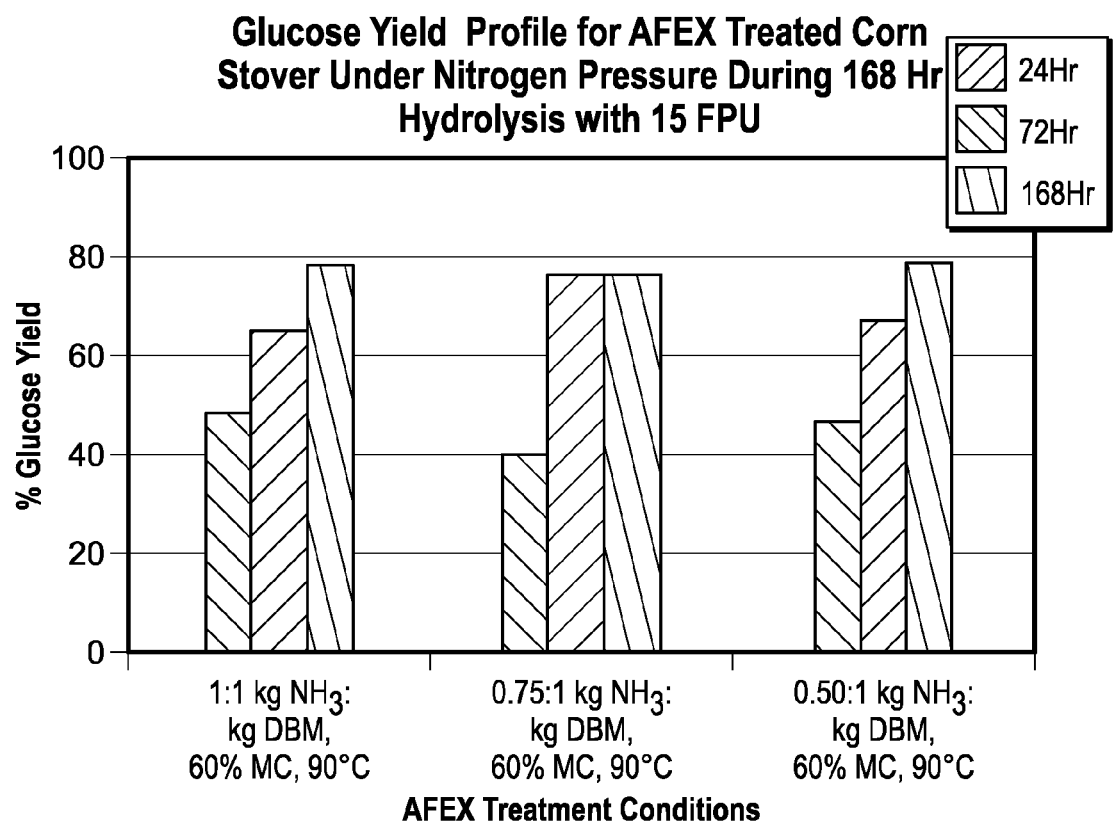
FIGS. 12 and 13 are graphs showing a glucose and xylose profile during 168 hr hydrolysis for different amounts of ammonia loading, respectively, according to various embodiments.
Figure 13:
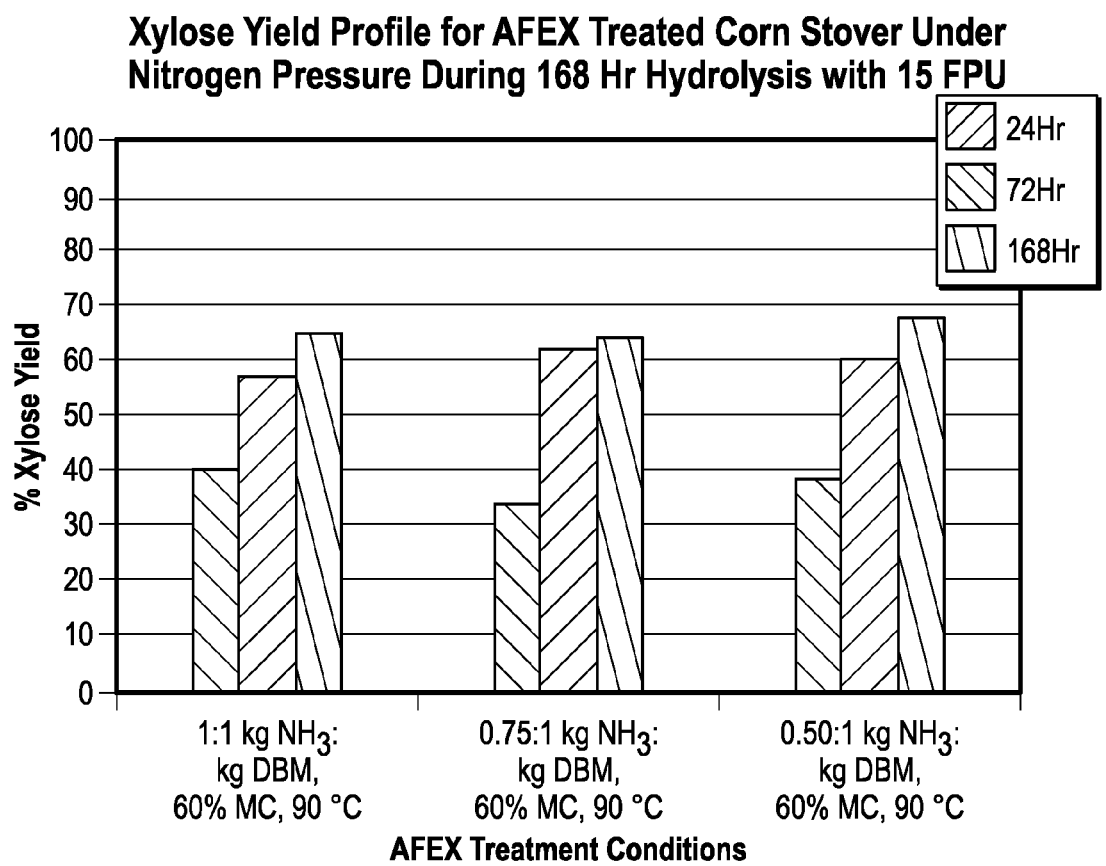

FIG. 10 shows the differences in yield as a result of differences in moisture content. As can be seen, while 40% moisture content gives a lower yield, 20% biomass moisture content (MC), by weight, yields better results a few percent higher than that of 60% MC, by weight. FIG. 11 shows differences in yield as a result of differences in ammonia loadings, with a trend similar to that shown in FIG. 10. Specifically, the lower MC of 20% produced a better result. FIGS. 12 and 13 show a glucose and xylose profile during a 168 hr hydrolysis for different amounts of ammonia loading, respectively. While both graphs show a similar hydrolysis rate, a ratio of 0.75 kg $NH_3$:1 kg dry biomass (DBM) is favored.

In the test results shown in FIG. 14 the overall glucose and xylose yields of two separate sets of conventional AFEX treated corn stover treatments under nitrogen pressure are shown. In the test results shown in FIG. 15, experiments were performed using varying ammonia loading at a fixed moisture content (60%, dwb) and temperature (90° C.), under nitrogen pressure. As the ammonia loading was lowered, a drop in conversion was observed after only after 0.3:1 ammonia to biomass loading. With respect to FIGS. 16A and 16B, the experiments were performed using two different ammonia to biomass ratio at fixed moisture content (60%) and temperature (90° C.), with and without nitrogen pressure. An increase in glucan and xylan conversion was observed when nitrogen pressure was increased in the reactor. The increase was similar for ammonia to biomass loadings of 0.5:1 and 0.75:1.

As a result, the third set of experiments was not conclusive, due possibly to poor hydrolysis. While not wishing to be bound by this proposed theory, it is possible that at the higher nitrogen overhead pressure, substantially all of the ammonia goes into a liquid phase such that more ammonia is in contact with the biomass.

Example 37

Pretreatment of Lignocellulosic Biomass Using Gaseous Ammonia

Figure 16A:
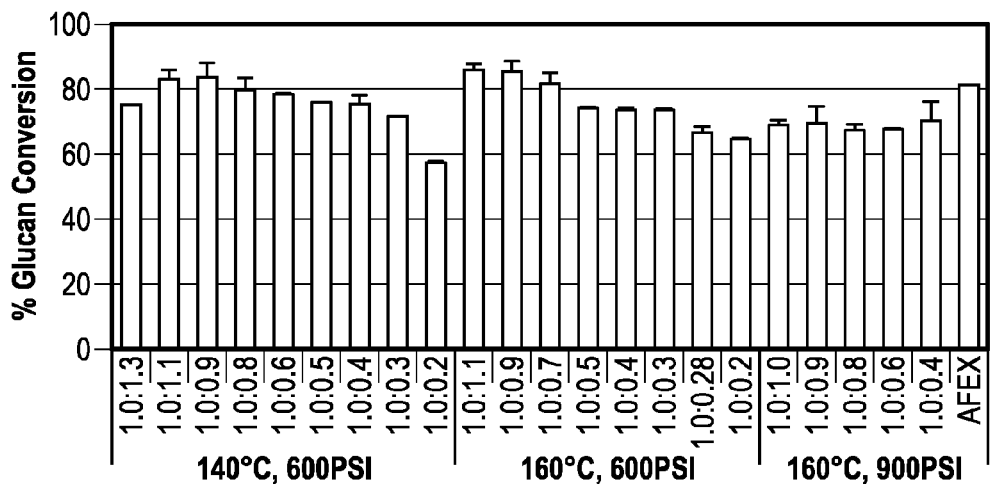
FIGS. 16A and 16B show percent glucose yield (% glucan conversion) from treated corn stover as a function of different GAP conditions according to various embodiments.

Anhydrous gaseous ammonia was transferred to a stainless steel cylinder and preheated to reach approximately 400 to about 900 psi (30.6 to 61.2 atm) (FIGS. 16A and B). In parallel, the biomass within the stainless steel reaction vessel ("reactor") with appropriate moisture (60%) was kept at different preheated temperatures for different experiments, namely, (at about 140° C. and about 160° C.). A vacuum was applied to remove air and to create negative pressure to facilitate ammonia delivery. The preheated ammonia gas was transferred to the reactor. The unreacted ammonia in the reactor was measured and the actual ammonia added to the pretreatment reactor during the process was calculated. There was a rapid rise in temperature of the biomass (from 30° C. initial temperature to about 100 to about 200° C.) depending on the pressure/temperature of preheated ammonia gas. The reaction was continued to achieve fixed residence times (15 minutes) and the pressure was then slowly released.

Example 38

Enzymatic Hydrolysis of Corn Stover Pretreated Using AFEX (Control) and GAP Process with Different Ammonia Loading and Residence Times The pretreated biomass was dried in the hood overnight and pretreatment efficiency was determined by digestion of the biomass with commercial enzymes (15 FPU of Spezyme CP from Genencor and 64 pNPGU of beta-glucosidase from Novozyme®, per g glucan) at 50° C. over a period of 72 hrs. The hydrolyzates were analyzed for glucose using YSI glucose analyzer.

As noted previously, FIG. 5 shows 5 and 15 minute reaction times using the GAP process, a 45 minute reaction time using the AFEX process, and various ratios of biomass to ammonia. Again, the data in FIG. 5 demonstrates equal or better pretreatment efficiency with GAP using significantly shorter reaction times than AFEX.

Example 39

Biomass Glucan Conversion as a Function of Different GAP Conditions

In order to further understand the effect of concentration of ammonia needed during the GAP process, the biomass moisture content was fixed at approximately 60% and the concentration of biomass to ammonia was varied from about 1:1.2 to about 1:0.2 (biomass to ammonia loading, w/w). In addition, the ammonia delivery pressure P1 (prior to loading) and reactor temperature were varied. These results are shown in FIGS. 16A and 16B.

Figure 16B:
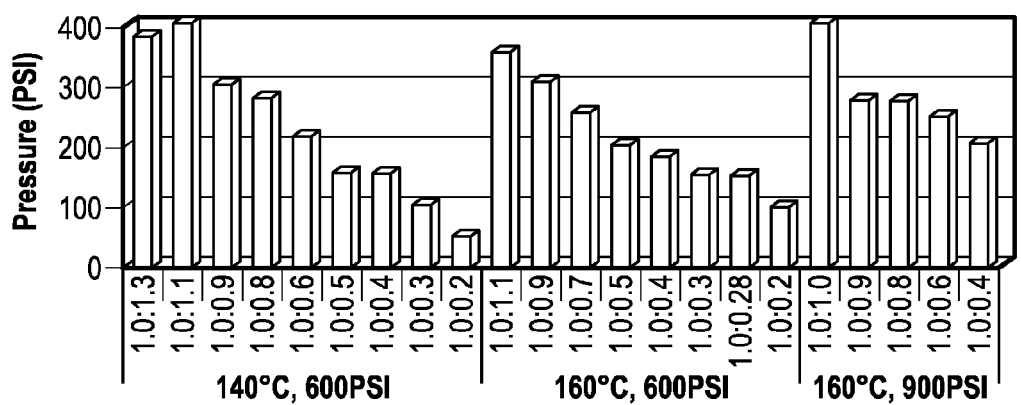

Specifically, FIGS. 16A and 16B show the percent glucose yield (% glucan conversion) from treated corn stover as a function of different GAP conditions, the effect of ammonia to biomass loading during the GAP process and the pretreatment effect seen during enzymatic hydrolysis (FIG. 16A) and pressure in the reactor during the process (FIG. 16B) according to various embodiments. In FIG. 16A, biomass to ammonia loading is shown on x-axis, which is examined at different pressures P1 and temperatures (of the gaseous ammonia before adding it to the reactor containing corn stover). Also in FIG. 16A, the y-axis gives the over glucose yield achieved as a function of various GAP conditions.

As FIGS. 16A and 16B show, a ratio of up to 1:0.8 for the conversions is comparable to conventional AFEX process (approximately: 60% moisture, 1:1 biomass to ammonia loading, and 45 min total residence time). By further dropping the biomass to ammonia loading (to about 1:0.2) there is only about a 10 to about 15% drop in glucose yield compared to the control. That is, there is nearly as much percent glucose conversion for GAP treated corn stover as AFEX treated corn stover at significantly lower ammonia loading and pressure in the reactor. In FIG. 16B, the y-axis in depicts the pressure in the reactor as a function of GAP conditions and shows that the pressure P2 in the reactor decreases with ammonia loading. By reducing the ammonia to biomass loading, the pressure in the reactor vessel also drops (FIG. 13) to between about 50 and about 150 psi (3.4 to 10.2 atm).

Although the glucose yield drops by 10%, the pressure P2 in the reactor vessel also drops below about 100 psi (6.8 atm). Hence, operational and capital costs for GAP carried out at lower pressure (and low ammonia loadings) will be substantially lower compared to AFEX and other ammonia based pretreatments. With the GAP process, by proper selection of an enzyme cocktail (containing suitable cellulases and hemicellulases), it is expected that conversion can be increased and processing costs reduced by further lowering biomass to ammonia loading (1:0.05 to about 1:0.2 biomass to ammonia loading, dwb) during the GAP process.

Example 40

Effect of Pressure Release During Pretreatment Process

Two independent pretreatments were performed using the AFEX and GAP process, utilizing an approximately 1:1 biomass to ammonia loading. In the first set of experiments the pressure was released rapidly. In the second set of experiments, the pressure was released slowly. In the rapid release, the pressure was suddenly reduced (under 1 second) from reaction pressure (about 200 to about 400 psi) (13.6 to 27.2 atm) to atmospheric pressure (about 15 psi) (1 atm). In the slow release experiment, the pressure was dropped gradually to atmospheric pressure (over a two-minute time period). The resultant feed stock was collected in a tray and dried in hood overnight. The next day, treated material was tested for digestibility using commercial enzymes at 50 C, for 72 hrs, as described above (FIG. 17).

Figure 17:
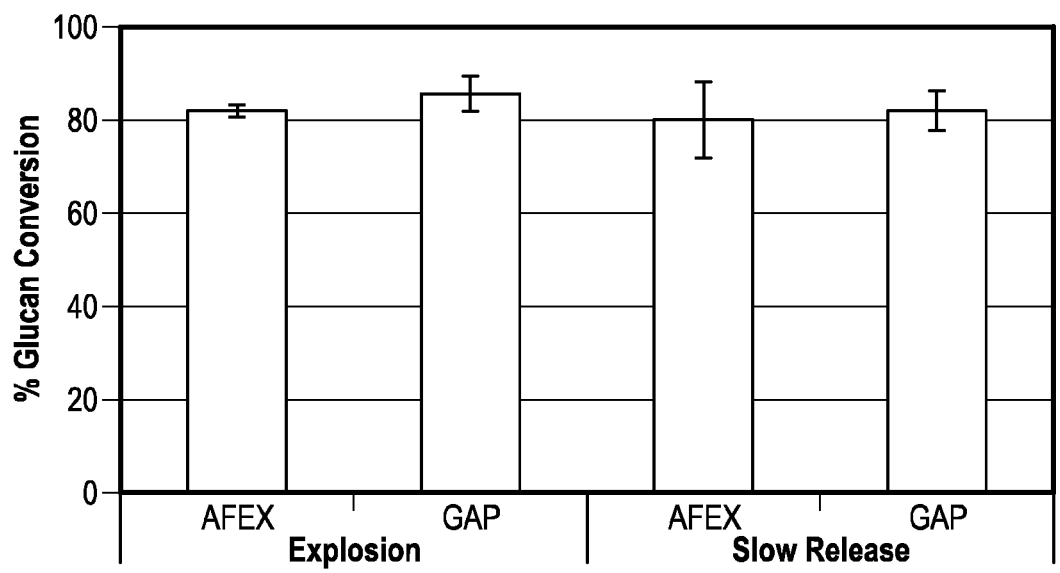
FIG. 17 shows the role of rapid removal of ammonia during conventional AFEX and GAP pretreatment process on glucose yield for treated corn stover according to various embodiments.

In FIG. 17 the y-axis depicts the % glucose yield (% glucan conversion) for differentially pretreated biomass samples. Marginal decreases in conversion for the pretreatment process performed were observed, with the slow release as compared with the rapid release. This decrease was within the error margin. This indicates that sudden expansion release of ammonia during pretreatment is likely not required. It is therefore possible to continuously pretreat the biomass fed continuously at a constant pressurized reactor fed with hot ammonia gas (and water) and/or inert/carrier gas mixtures.

Example 41

Hydrolysis for Untreated and AFEX-Treated Corn Stover

In order to demonstrate that low moisture biomass (5%, dwb) gives comparable pretreatment results to that of high moisture biomass (60%, dwb), a pretreatment was performed for these conditions and enzymatic hydrolysis using 15 FPU of cellulase and 64 pNPGU of beta-glucosidase. The conversion results are shown in FIG. 7.

FIG. 7, discussed above, shows hydrolysis for untreated and AFEX-treated corn stover. Regular AFEX was performed at 90° C., 1:1 biomass to ammonia loading (60%, dwb) at 5 min residence time; and low moisture AFEX was performed at 90° C., 1:1 biomass to ammonia loading (5%, dwb) at 5 min residence time after 24 hours of incubation at 50° C. at 200 rpm. The y-axis depicts the glucose and xylose yields after enzymatic hydrolysis for the various pretreatment conditions.

Figure 18A:
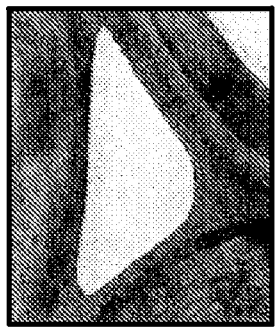
FIGS. 18A-18D show transmission electron micrograph images of untreated (FIG. 18A), low moisture conventional AFEX treated (FIG. 18B) corn stover cell walls and magnifications of varying portions of the low moisture conventional AFEX treated samples (FIGS. 18C and 18D) according to various embodiments.
Figure 18B:

In addition, electron tomographic images showed that pretreating biomass with low moisture creates more porosity within the cell wall than when using higher moisture content (FIGS. 18A and 18B). See, Shishir P.S., et al., Multi-scale visualization and characterization of lignocellulosic plant cell wall deconstruction during thermochemical pretreatment, *Energy Environ. Sci.*, 4, 973-984 (2011). The increased porosity allows for better accessibility for the enzymes to hydrolyze pretreated biomass more efficiently.

Figure 18C:
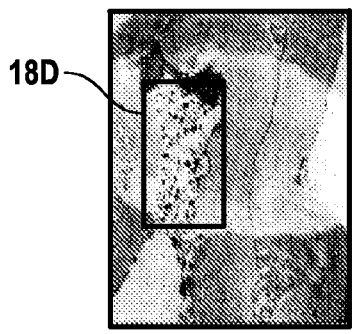
Figure 18D:

The slightly lower conversion for low moisture AFEX treated sample could be due to lack of suitable hemicellulases during enzymatic hydrolysis and poor heat/mass transfer during AFEX pretreatment. FIGS. 18C and 18D show magnifications of varying portions of the low moisture conventional AFEX treated samples.

By proper control of the above-mentioned factors together with GAP-based fluidization, even better results may be obtained. One advantage of low moisture ammonia based treatments, especially during GAP, is the demonstrated easier recovery of ammonia from water. That is, when more water is in the system, more expense is needed to recover (and recycle) ammonia from the system.

Example 42

Comparison of Resource Savings and GHG Emissions

In order to evaluate the energy, resources saving and greenhouse gas emissions (GHG) for the GAP process, when compared to conventional AFEX process, a calculation based on an Aspen plus model (initially developed at National Renewable Energy Laboratory (NREL), Golden, Colo., Eggeman and Elander, 2005, now with further adaptations) more details on the software was performed. Using the Aspen software and the basic modeling approach developed by NREL, it was possible to remove and re-insert individual pieces of the model, thereby making "upgrades" to allow for possible technology developments. In this testing, some model alterations were made that included eliminating feedstock washing, including an innovative ammonia recovery approach, and raising the feedstock feed rate to approximately 5000 tons dry biomass/day (907 kg).

The results are shown in Table 2. These results show a substantial amount of heat, electricity and water saving, in addition to a 3-fold reduction in GHG emissions for the GAP process.

TABLE 2

| | Process information | | | GHG | |
|---|---|---|---|---|---|
| | unit | GAP | AFEX | unit | GAP | AFEX |
| Corn stover | Mt | 1 | 1 | | | |
| Ammonia | kg | 8.8 | 8.8 | kg | 24 | 25 |
| Water | kg | 0 | 896 | kg | 0 | 1 |
| Electricity | MJ | 19 | 33 | kg | 4 | 7 |
| Heat | MJ | 449 | 2521 | kg | 35 | 194 |
| Biomass | Mt | 1 | 1 | | | |
| Total | | | | | 63 | 226 |

CONCLUSION

Various embodiments described herein provide a process for the treatment of a plant biomass to increase the reactivity of polysaccharides, comprising hemicellulose and cellulose as compared to polysaccharides in biomass which has not been pretreated. In one embodiment, plant biomass having varying moisture contents is ground and contacted with ammonia in the liquid or vapor state, and/or concentrated ammonia/water mixtures in the liquid or vapor state, to obtain a mixture having a particular ratio. The components are then allowed to react at a desired temperature, for a period of time, until pretreated biomass is produced.

In one embodiment, the pretreated biomass is thereafter extracted to remove lignin and other compounds that can interfere with the ability of enzymes to hydrolyze the pretreated biomass and/or the ability of microorganisms to ferment the pretreated biomass. In one embodiment, the pretreated biomass is hydrolyzed with enzymes to produce sugars and the sugars are fermented by a microorganism to produce a fermentation product. In one embodiment, no separate sugar production step is used. In one embodiment, the pretreated biomass is consumed by an animal. In one embodiment, the plant biomass is fermented to produce a biofuel, such as ethanol.

Conventional ammonia-based pretreatment processes use dilute ammonia (ammonium hydroxide), the embodiments described herein use gaseous ammonia (with the exception of the optimized AFEX treatment which utilizes conventional AFEX conditions for the reaction, but includes a novel ammonia recovery system and process). The known dilute ammonia processes generally use about 15% to 30% ammonium hydroxide. As noted herein, residence time is dependent on temperature, with lower temperatures having a longer residence time and higher temperatures having a shorter residence time.

In contrast, the GAP process discussed herein, can utilize an ammonia to biomass ratio of about 1:1.3 down to about 1:0.2 (See FIG. 16A). In one embodiment, the conversion ratio is about 1:1.1 to about 1:0.6 exhibits a high conversion. Testing with 60% and 8% moisture MC (dwb) (i.e., the ammonia to water ratio) resulted in comparable conversions and 8% (similar to FIG. 7). Operating temperatures in the GAP process can be achieved instantaneously due to the reaction of ammonia with water, and are therefore, once the ratios and other parameters have been set, temperature is not a controlled reaction variable. In one embodiment, the temperature rises to about 14° C. Under another set of conditions, the temperature can rise to about 16° C., with substantially identical results achieved. Residence times in the GAP process can vary. See, for example, FIG. 5, in which residence times were performed at 5 and 15 minutes.

All publications, patents and patent documents are incorporated by reference herein, as though individually incorporated by reference, each in their entirety, as though individually incorporated by reference. In the case of any inconsistencies, the present disclosure, including any definitions therein, will prevail.

Although specific embodiments have been illustrated and described herein, it will be appreciated by those of ordinary skill in the art that any procedure that is calculated to achieve the same purpose may be substituted for the specific embodiments shown. This application is intended to cover any adaptations or variations of the present subject matter. Therefore, it is manifestly intended that embodiments of this invention be limited only by the claims and the equivalents thereof.

What is claimed is:

1. A method for pretreating lignocellulosic biomass comprising:
   adding gaseous ammonia to a pressurized reactor containing lignocellulosic biomass wherein the gaseous ammonia is added to the reactor at a pressure from about 6.8 to about 50 atm;
   allowing the gaseous ammonia to condense on the biomass and react with water present in the biomass to produce pretreated biomass, wherein the pressure of the reactor is released to about atmospheric pressure, and reactivity of polysaccharides present in the biomass is increased during subsequent biological conversion as compared to the reactivity of polysaccharides present in biomass which has not been pretreated; and removing residual ammonia present in the reaction vessel.

2. The method of claim 1 wherein the subsequent biological conversion comprises enzyme hydrolysis or ruminant digestibility; and the method further comprises adding water to the biomass.

3. The method of claim 1 wherein the polysaccharides include hemicellulose and cellulose and the reactivity is at least about 60% conversion of the hemicellulose and about 70% conversion of the cellulose to fermentable sugars within 24 hrs or less.

4. The method of claim 1 wherein the temperature in the reactor increases substantially instantaneously when the water and gaseous ammonia react and upon further processing more than about 29.5% up to about 80% of glucan and xylan in the pretreated biomass is converted to glucose and xylose, respectively, within three days or less.

5. The method of claim 4 wherein the reactor temperature is from about 50° C. to about 140° C.

6. The method of claim 1 wherein the reactor temperature is from about 100° C. to about 140° C.

7. The method of claim 1 wherein the gaseous ammonia is added to the reactor at a pressure from about 6.8 atm to about 20.4 atm.

8. The method of claim 1 wherein the biomass is comprised of from about 5% to about 233% water on a dry weight basis.

9. The method of claim 1 wherein the biomass is comprised of from about 5% to about 60% water on a dry weight basis.

10. The method of claim 1 wherein the gaseous ammonia reacts with the water in the biomass for about 1 minute to about 120 minutes.

11. The method of claim 9 wherein the gaseous ammonia reacts with the water in the biomass for about 1 minute to about 20 minutes.

12. The method of claim 1 wherein the method is a continuous method.

13. The method of claim 1 further comprising recycling at least a portion of the gaseous ammonia.

14. The method of claim 1 wherein the method is a semi-continuous method.

15. A method for pretreating lignocellulosic biomass comprising:
    in a pressurized reactor, impregnating biomass with an amount of gaseous ammonia sufficient to initiate a reaction, wherein the biomass contains water wherein the gaseous ammonia is added to the reactor at a pressure from about 6.8 to about 50 atm;
    releasing pressure in the reactor to about atmospheric pressure to produce pretreated biomass;
    allowing a gaseous carrier delivered to the reactor at an elevated temperature to remove residual ammonia in the biomass to produce pretreated biomass substantially free from ammonia, and
    recycling the residual ammonia, wherein the amount of ammonia utilized is reduced as compared to a process of pretreating lignocellulosic biomass with no recycling.

16. The method of claim 15 further comprising removing the pretreated biomass from the reactor.

17. The method of claim 2 further comprising impregnating the biomass with ammonia prior to the allowing and/or delivering steps.

18. The method of claim 1 wherein the pressure of the reactor is released over a two-minute time period.

* * * * *

UNITED STATES PATENT AND TRADEMARK OFFICE
CERTIFICATE OF CORRECTION

PATENT NO. : 9,644,222 B2
APPLICATION NO. : 13/997043
DATED : May 9, 2017
INVENTOR(S) : Venkatesh Balan et al.

It is certified that error appears in the above-identified patent and that said Letters Patent is hereby corrected as shown below:

On the Title Page

Page 3/In the References, Other Publications/Column 2/Carolan: Error reads as "Carolan, etal" and should read as "Carolan, et al.,"

In the Specification

Column 5/Line 65: Error reads as "Optimal Enzyme Coktail:" and should read as "Optimal Enzyme Cocktail:"

Column 6/Lines 64-65: Error reads as "As can be seen, many known ammonia pretreatment methods pretreatment temperatures" and should read as "As can be seen, many known ammonia pretreatment methods use pretreatment temperatures"

Column 12/Lines 13-14: Error reads as "With a smaller the particle size, however," and should read as "With a smaller particle size, however,"

Column 16/Lines 8-9: Error reads as "steal beads" and should read as "steel beads"

Column 21/Lines 56-57: Error reads as "In FIG. 16B, the y-axis in depicts" and should read as "In FIG. 16B, the y-axis depicts"

Column 23/Lines 26-27: Error reads as "now with further adaptations) more details" and should be read as "now with further adaptations, provides more details"

Column 24/Line 32: Error reads as "water, and are therefore," and should read as "water. Therefore,"

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,644,222 B2

In the Claims

Column 26/Claim 15/Lines 25-26: Error reads as "with no recycling." and should read as "with no recycling of ammonia."